United States Patent
Holland et al.

(10) Patent No.: US 10,268,053 B2
(45) Date of Patent: Apr. 23, 2019

(54) UV/VISIBLE-ABSORBING VINYLIC MONOMERS AND USES THEREOF

(71) Applicant: Novartis AG, Basel (CH)

(72) Inventors: Troy Vernon Holland, Suwanee, GA (US); Frank Chang, Cumming, GA (US); Walter R. Laredo, Forth Worth, TX (US); Xuwei Jiang, Arlington, TX (US); Ryan DeSousa, Atlanta, GA (US)

(73) Assignee: Novartis AG, Basel (CH)

( * ) Notice: Subject to any disclaimer, the term of this patent is extended or adjusted under 35 U.S.C. 154(b) by 137 days.

(21) Appl. No.: 15/434,098

(22) Filed: Feb. 16, 2017

(65) Prior Publication Data

US 2017/0242274 A1    Aug. 24, 2017

Related U.S. Application Data

(60) Provisional application No. 62/298,124, filed on Feb. 22, 2016.

(51) Int. Cl.

| | |
|---|---|
| *C07C 233/23* | (2006.01) |
| *G02C 7/10* | (2006.01) |
| *C07C 233/33* | (2006.01) |
| *C08F 283/12* | (2006.01) |
| *G02B 1/04* | (2006.01) |
| *G02C 7/04* | (2006.01) |
| *C07C 225/22* | (2006.01) |
| *C07C 237/32* | (2006.01) |
| *C07C 237/34* | (2006.01) |

(52) U.S. Cl.
CPC ............ *G02C 7/108* (2013.01); *C07C 225/22* (2013.01); *C07C 233/33* (2013.01); *C07C 237/32* (2013.01); *C07C 237/34* (2013.01); *C08F 283/124* (2013.01); *G02B 1/043* (2013.01); *G02C 7/049* (2013.01)

(58) Field of Classification Search
CPC .................................................. C07C 233/33
See application file for complete search history.

(56) References Cited

U.S. PATENT DOCUMENTS

| | | |
|---|---|---|
| 4,136,250 A | 1/1979 | Mueller et al. |
| 4,153,641 A | 5/1979 | Deichert et al. |
| 4,182,822 A | 1/1980 | Chang et al. |
| 4,189,546 A | 2/1980 | Deichert et al. |
| 4,254,248 A | 3/1981 | Friends et al. |
| 4,259,467 A | 3/1981 | Keogh et al. |
| 4,260,725 A | 4/1981 | Keogh et al. |
| 4,261,875 A | 4/1981 | LeBoeuf |
| 4,276,402 A | 6/1981 | Chromecek et al. |
| 4,327,203 A | 4/1982 | Deichert et al. |
| 4,341,889 A | 7/1982 | Deichert et al. |
| 4,343,927 A | 8/1982 | Chang |
| 4,355,147 A | 10/1982 | Deichert et al. |
| 4,390,676 A | 6/1983 | Loshaek |
| 4,444,711 A | 4/1984 | Schad |
| 4,460,534 A | 7/1984 | Boehm et al. |
| 4,486,577 A | 12/1984 | Mueller et al. |
| 4,528,311 A | 7/1985 | Beard et al. |
| 4,543,398 A | 9/1985 | Angelini et al. |
| 4,605,712 A | 8/1986 | Mueller |
| 4,661,575 A | 4/1987 | Tom |
| 4,684,538 A | 8/1987 | Klemarczyk |
| 4,703,097 A | 10/1987 | Wingler et al. |
| 4,716,234 A | 12/1987 | Dunks et al. |
| 4,803,254 A | 2/1989 | Dunks et al. |
| 4,833,218 A | 5/1989 | Lee |
| 4,837,289 A | 6/1989 | Mueller |
| 4,954,586 A | 9/1990 | Toyoshima et al. |
| 4,954,587 A | 9/1990 | Mueller |
| 4,998,817 A | 3/1991 | Zeltzer |
| 5,010,141 A | 4/1991 | Sharma et al. |
| 5,034,461 A | 7/1991 | Lai et al. |
| 5,039,761 A | 8/1991 | Ono et al. |
| 5,070,170 A | 12/1991 | Robertson |
| 5,079,319 A | 1/1992 | Mueller |
| 5,235,358 A | 8/1993 | Mutzhas |
| 5,346,946 A | 9/1994 | Yokoyama et al. |
| 5,358,995 A | 10/1994 | Kunzler et al. |
| 5,387,632 A | 2/1995 | Lai et al. |
| 5,416,132 A | 5/1995 | Yokoyama et al. |
| 5,451,617 A | 9/1995 | Lai et al. |
| 5,470,932 A | 11/1995 | Jinkerson |

(Continued)

FOREIGN PATENT DOCUMENTS

| | | |
|---|---|---|
| CA | 1318755 C | 6/1993 |
| EP | 0274844 B1 | 11/1991 |

(Continued)

OTHER PUBLICATIONS

Nishio, et al.; "A novel intramolecular photocyclization of N-(2-bromoalkanoyl) derivatives of 2-acylanilines via 1,8-hydrogen abstraction"; Helvetica Chimica Acta; vol. 88; 2005; pp. 996-1003.

Tanito, et al.; "Protective effects of soft acrylic yellow filter against blue light-induced retinal damage in rats"; Experimental Eye Research; vol. 83; 2006; pp. 1493-1504.

Kernt, et al.; Cytoprotective effects of a blue light-filtering intraocular lens on human retinal pigment epithelium by reducing phototoxic effects on vascular endothelial growth factor-a, Bax, and Bcl-2 expression; J. Cataract Refractive Surgery; 2009, vol. 35; pp. 354-362.

Rezai, et al.; "AcrySof natural filter decreases blue light-induced apoptosis in human retinal pigment epithelium"; Graefe's Arch Clin Exp Ophthalmol; 2008; vol. 246; pp. 671-676.

(Continued)

*Primary Examiner* — Michael F Pepitone
(74) *Attorney, Agent, or Firm* — Jian Zhou

(57) ABSTRACT

Described herein are UV-absorbing vinylic monomers and their uses in preparing UV-absorbing contact lenses capable of blocking ultra-violet ("UV") radiation and violet radiation with wavelengths from 380 nm to 440 nm, thereby protecting eyes to some extent from damages caused by UV radiation and potentially from violet radiation.

9 Claims, 1 Drawing Sheet

(56) References Cited

U.S. PATENT DOCUMENTS

| | | |
|---|---|---|
| 5,486,579 A | 1/1996 | Lai et al. |
| 5,487,885 A | 1/1996 | Sovak et al. |
| 5,543,504 A | 8/1996 | Jinkerson |
| 5,583,163 A | 12/1996 | Mueller Beat |
| 5,592,245 A | 1/1997 | Moore et al. |
| 5,617,154 A | 4/1997 | Hoffman |
| 5,625,427 A | 4/1997 | Araujo et al. |
| 5,637,726 A | 6/1997 | Collins et al. |
| 5,665,840 A | 9/1997 | Pohlmann et al. |
| 5,712,356 A | 1/1998 | Bothe et al. |
| 5,741,924 A | 4/1998 | Sovak et al. |
| 5,760,100 A | 6/1998 | Nicolson et al. |
| 5,838,419 A | 11/1998 | Holland |
| 5,843,346 A | 12/1998 | Morrill |
| 5,849,841 A | 12/1998 | Muhlebach et al. |
| 5,866,635 A | 2/1999 | Collins et al. |
| 5,894,002 A | 4/1999 | Boneberger et al. |
| 5,962,548 A | 10/1999 | Vanderlaan et al. |
| 5,975,695 A | 11/1999 | Baiocchi |
| 5,981,675 A | 11/1999 | Valint et al. |
| 6,039,913 A | 3/2000 | Hirt |
| 6,132,044 A | 10/2000 | Sternbergh |
| 6,165,408 A | 12/2000 | Steinmann |
| 6,221,303 B1 | 4/2001 | Steinmann |
| 6,303,687 B1 | 10/2001 | Mueller Beat |
| 6,305,801 B1 | 10/2001 | Kerns et al. |
| 6,420,290 B1 | 7/2002 | Brocheton et al. |
| 6,432,137 B1 | 8/2002 | Nanushyan |
| 6,472,489 B1 | 10/2002 | Stockinger |
| 6,479,587 B1 | 11/2002 | Stockinger |
| 6,492,478 B1 | 12/2002 | Steinmann |
| 6,627,124 B1 | 9/2003 | Herbrechtsmeier et al. |
| 6,641,261 B2 | 11/2003 | Wang |
| 6,762,264 B2 | 7/2004 | Kuenzler et al. |
| 6,800,225 B1 | 10/2004 | Hagmann et al. |
| 6,811,727 B2 | 11/2004 | Havens et al. |
| 6,955,430 B2 | 10/2005 | Pratt |
| 6,995,192 B2 | 2/2006 | Phelan et al. |
| 7,091,283 B2 | 8/2006 | Mueller et al. |
| 7,238,750 B2 | 7/2007 | Mueller et al. |
| 7,255,435 B2 | 8/2007 | Pratt |
| 7,268,189 B2 | 9/2007 | Mueller et al. |
| 7,276,544 B2 | 10/2007 | Lai et al. |
| 7,278,737 B2 | 10/2007 | Mainster et al. |
| 7,364,291 B2 | 4/2008 | Haywood et al. |
| 7,384,590 B2 | 6/2008 | Kelly et al. |
| 7,387,759 B2 | 6/2008 | Kelly et al. |
| 7,520,607 B2 | 4/2009 | Casper et al. |
| 7,520,608 B2 | 4/2009 | Ishak et al. |
| 7,521,519 B1 | 4/2009 | Hirt et al. |
| 7,524,060 B2 | 4/2009 | Sanchez Ramos |
| 7,556,376 B2 | 7/2009 | Ishak |
| 7,605,190 B2 | 10/2009 | Moszner et al. |
| 7,703,917 B2 | 4/2010 | Sanchez Ramos |
| 7,748,845 B2 | 7/2010 | Casper et al. |
| 7,771,470 B2 | 8/2010 | Mentak |
| 7,825,257 B1 | 11/2010 | Deo et al. |
| 7,842,367 B2 | 11/2010 | Mentak |
| 7,857,848 B2 | 12/2010 | Mentak |
| 7,884,228 B1 | 2/2011 | Laredo |
| 7,915,323 B2 | 3/2011 | Awasthi et al. |
| 7,947,849 B2 | 5/2011 | Laredo |
| 7,977,430 B2 | 7/2011 | Devlin et al. |
| 8,047,650 B2 | 11/2011 | Mainster et al. |
| 8,096,656 B2 | 1/2012 | Giraudet |
| 8,113,651 B2 | 2/2012 | Blum et al. |
| 8,153,703 B2 | 4/2012 | Laredo |
| 8,192,020 B2 | 6/2012 | Giraudet |
| 8,207,244 B2 | 6/2012 | Laredo |
| 8,232,326 B2 | 7/2012 | Laredo |
| 8,262,947 B2 | 9/2012 | Laredo |
| 8,262,948 B2 | 9/2012 | Laredo et al. |
| 8,329,775 B2 | 12/2012 | Laredo |
| 8,360,574 B2 | 1/2013 | Ishak et al. |
| 8,403,478 B2 | 3/2013 | Ishak |
| 8,420,711 B2 | 4/2013 | Awasthi et al. |
| 8,475,691 B2 | 7/2013 | Laredo |
| 8,500,274 B2 | 8/2013 | Ishak |
| 8,585,938 B1 | 11/2013 | Jinkerson et al. |
| 8,877,103 B2 | 11/2014 | Alvarez-Carrigan et al. |
| 8,882,267 B2 | 11/2014 | Ishak et al. |
| 2006/0252844 A1 | 11/2006 | Mentak |
| 2006/0252850 A1 | 11/2006 | Jani et al. |
| 2007/0004852 A1 | 1/2007 | Mentak |
| 2007/0004863 A1 | 1/2007 | Mentak |
| 2007/0092830 A1 | 4/2007 | Lai et al. |
| 2007/0092831 A1 | 4/2007 | Lai et al. |
| 2008/0015315 A1 | 1/2008 | Chang et al. |
| 2008/0143003 A1 | 6/2008 | Phelan |
| 2008/0143958 A1 | 6/2008 | Medina et al. |
| 2008/0231798 A1 | 9/2008 | Zhou et al. |
| 2008/0234457 A1 | 9/2008 | Zhou et al. |
| 2010/0041787 A1 | 2/2010 | Chen |
| 2010/0296049 A1 | 11/2010 | Justynska et al. |
| 2010/0298446 A1 | 11/2010 | Chang et al. |
| 2011/0075096 A1 | 3/2011 | Ishak et al. |
| 2011/0157546 A1 | 6/2011 | Ishak et al. |
| 2012/0075577 A1 | 3/2012 | Ishak et al. |
| 2012/0088843 A1 | 4/2012 | Chang et al. |
| 2012/0088844 A1 | 4/2012 | Kuyu et al. |
| 2012/0244088 A1 | 9/2012 | Saxena et al. |
| 2012/0245249 A1 | 9/2012 | Saxena et al. |
| 2013/0282115 A1 | 10/2013 | Ishak |
| 2014/0055736 A1 | 2/2014 | Ishak |
| 2014/0233105 A1 | 8/2014 | Schmeder et al. |
| 2014/0300857 A1 | 10/2014 | Cohen Tannoudji et al. |
| 2014/0362339 A1* | 12/2014 | Imafuku .............. G02B 1/043 351/159.33 |
| 2015/0098058 A1 | 4/2015 | De Ayguavives et al. |
| 2015/0103310 A1 | 4/2015 | De Ayguavives et al. |
| 2015/0234208 A1 | 8/2015 | De Ayguavives et al. |
| 2015/0370094 A1 | 12/2015 | Hashimoto et al. |
| 2016/0017218 A1 | 1/2016 | Kojima et al. |
| 2016/0304701 A1 | 10/2016 | Kakinuma et al. |
| 2016/0313575 A1 | 10/2016 | Kakinuma et al. |
| 2016/0357031 A1 | 12/2016 | Holland et al. |

FOREIGN PATENT DOCUMENTS

| | | | |
|---|---|---|---|
| EP | 0632329 A1 | 1/1995 | |
| JP | S62230759 | 10/1987 | |
| JP | H06207142 A | 7/1994 | |
| WO | 2007/050395 A2 | 5/2007 | |
| WO | 2011/130138 A1 | 10/2011 | |
| WO | 2013/188825 A1 | 12/2013 | |
| WO | 2014/011581 A2 | 1/2014 | |
| WO | 2014/018208 A1 | 1/2014 | |
| WO | WO-2014003714 A1 * | 1/2014 | ............... C08K 5/18 |

OTHER PUBLICATIONS

Algvere, et al.; "Age-related maculopathy and the impact of blue light hazard" Acta Ophthalmologica Scandinavica; 2006; vol. 84; pp. 4-15.

Mainster; "Violet and blue light blocking intraocular lenses: photoprotection versus photoreception"; Br. J. Ophthalmol 2006; vol. 90; pp. 784-792.

Park, et al.; "Improved loading and cleavage methods for solid-phase synthesis using chlorotrityl resins: synthesis and testing of a library of 144 discrete chemicals as potential farnesyltransferase inhibitors"; Journal of Combinatorial Chemistry; American Chemical Society; 2004; vol. 6, No. 3; pp. 407-413.

Kosasayama, et al.; Cyclic guanidines. VI.(1) synthesis of hypoglycemic tricyclic guanidines; Chem. Pharm. Bull; 1979; vol. 27, No. 4; pp. 880-892.

Zhou, et al.; "Light filtering in a retinal pigment epithelial cell culture model"; Optometry and Vision Science; American Academy of Optometry; 2011; vol. 88; No. 6; pp. 759-765.

Database WPI; Week 198746, Thomson Scientific, London, GB; AN 1987-324524, XP002769134 and JPS62230759; Nippon Shokubai Kagaku Kogyo, Co. Ltd.; Abstract translation only.

(56) References Cited

OTHER PUBLICATIONS

Database CA; Chemical Abstracts Service, Columbus, Ohio, US; Nakagawa, Hiroo et al: "Polyurethane coating compositions with excellent weatherability", XP002769135, retrieved from STN Database accession No. 1995:169562 abstract and JPH06207142; Nippon Catalytic Chem. Ind., Jul. 26, 1994; Machine translation.

* cited by examiner

UV/VISIBLE-ABSORBING VINYLIC MONOMERS AND USES THEREOF

This application claims the benefits under 35 USC § 119 (e) of U.S. provisional application No. 62/298,124 filed 22 Feb. 2016, herein incorporated by reference in its entirety.

This invention is related to amino benzophenone vinylic monomers capable of absorbing ultra-violet (UV) radiation and high-energy-violet (HEVL) radiation and their uses for producing hydrogel contact lenses capable of blocking ultraviolet ("UV") radiation and violet radiation with wavelengths from 380 nm to 440 nm from a water-based hydrogel lens formulation.

BACKGROUND

The health risks of UVA and UVB light to the human eye and skin have been well documented. Recently short wavelength visible light, both violet and blue, were shown to be damaging to cells both in in vitro and in vivo studies reported in Experimental Eye Research 2006, 83, 1493; J. Cataract Refrac Surg 2009, 35, 354; Graefe's Arch Clin Exp Ophthalmol 2008, 246, 671; Acta Ophthalmologica Scandinavica 2006, 84, 4; Br J Ophthalmol 2006, 90, 784; Optometry and Vision Science 2011, 88(6), 1 (herein incorporated by references in their entireties). It would be advantageous to have violet and blue light blocking contact lenses which can block some light in the region of 380 nm to 460 nm.

UV absorbers are known as ingredients for polymeric materials used to make ophthalmic lenses. Such absorbers are preferably polymerizable so as to be covalently bound to the polymeric network of the lens material instead of simply physically entrapped in the material, thereby preventing them from migrating, phase separating or leaching out of the lens material. Such stability is particularly important for ophthalmic lenses because the leaching of the absorber may present both toxicological issues and lead to the loss of UV/visible blocking activity of the ophthalmic lenses.

Polymerizable benzatriazole, benzophenone and triazine absorbers are known. Most of these compounds are known as UV absorbers, though some may be known to also absorb some portion of visible light. Many absorbers contain ethylenically unsaturated groups, such as methacrylate, acrylate, methacrylamide, acrylamide or styrene groups. Copolymerization with other ingredients in the lens materials incorporates the absorbers into the resulting polymer chain.

U.S. Pat. Nos. 8,153,703, 8,232,326, 8,262,947, and 8,585,938 (herein incorporated by references in their entireties) disclose benzotriazole vinylic monomers which can block HEVL. Although the benzotriazoles vinylic monomers are typically photo-stable and can absorb a large amount of both visible and UV light, they may be difficult and expensive to make. Also, they may not be soluble in a lens formulation. If the absorber does not have sufficient solubility in a lens formulation, the absorber may coalesce into domains that could interact with light and result in decreased optical clarity of the lens.

WO2014/018208 (herein incorporated by reference in its entirety) recently discloses new UV/visible light absorbing vinylic monomers with anthraquinone structures. Anthroquinone vinylic monomers may not have a desired photostability for use in ophthalmic lenses.

There is a need for a visible light absorbing vinylic monomer that absorbs lights between 380 and 460 nm, shows good solubility in formulations, is photo-stable, and is inexpensive to make.

SUMMARY

In one aspect, the invention provides an UV-absorbing vinylic monomer comprising a moiety of amino benzophenone and a (meth)acryloyl group.

In another aspect, the invention provides a method for producing UV-absorbing contact lenses from a lens formulation comprising a UV-absorbing vinylic monomer of the invention.

The invention provides in a further aspect hydrogel contact lenses comprising monomeric units of an UV-absorbing vinylic monomer of the invention.

DETAILED DESCRIPTION

Figure 1A:
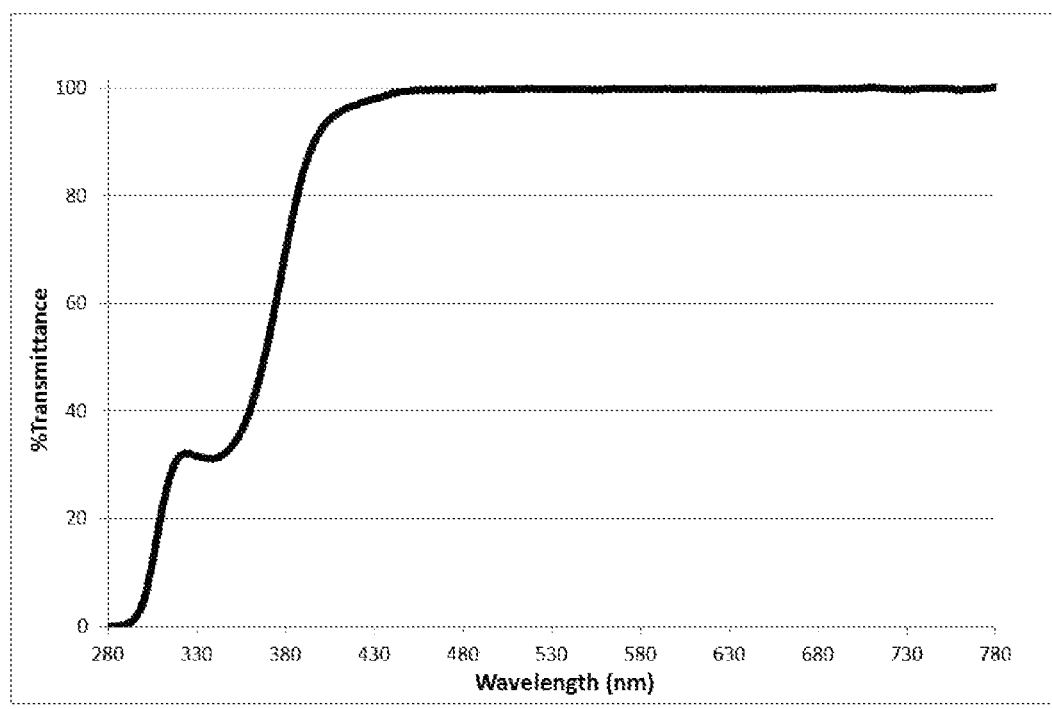
FIG. 1A shows the UV/Vis spectra of a contact lens containing an UV-absorbing vinylic monomer of the invention according to preferred embodiment.

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well-known and commonly employed in the art.

"About" as used herein means that a number referred to as "about" comprises the recited number plus or minus 1-10% of that recited number.

"Optional" or "optionally" means that the subsequently described event or circumstance can or cannot occur, and that the description includes instances where the event or circumstance occurs and instances where it does not.

A "contact Lens" refers to a structure that can be placed on or within a wearer's eye. A contact lens can correct, improve, or alter a user's eyesight, but that need not be the case.

As used in this application, the term "hydrogel" or "hydrogel material" refers to a crosslinked polymeric material which is insoluble in water, but can hold at least 10 percent by weight of water in its three-dimensional polymer networks (i.e., polymer matrix) when it is fully hydrated.

A "vinylic monomer" refers to a compound that has one sole ethylenically-unsaturated group.

The term "soluble", in reference to a compound or material in a solvent, means that the compound or material can be dissolved in the solvent to give a solution with a concentration of at least about 0.1% by weight at room temperature (i.e., from about 20° C. to about 30° C.).

The term "insoluble", in reference to a compound or material in a solvent, means that the compound or material can be dissolved in the solvent to give a solution with a concentration of less than 0.005% by weight at room temperature (as defined above).

The term "ethylenically unsaturated group" is employed herein in a broad sense and is intended to encompass any groups containing at least one >C=C< group. Exemplary ethylenically unsaturated groups include without limitation (meth)acryloyl

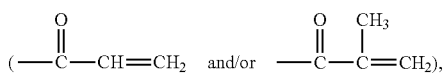

allyl, vinyl (—CH=CH$_2$), 1-methylethenyl

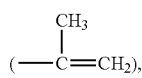

styrenyl, or the likes.

The term "(meth)acryloylamido group" refers to a radical of

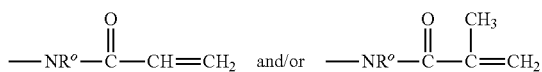

in which R$^o$ is hydrogen or a C$_1$-C$_6$ alkyl.

The term "(meth)acryloyloxy group" refers to a radical of

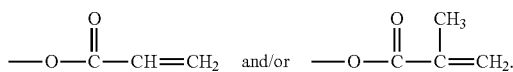

The term "(meth)acrylamide" refers to methacrylamide and/or acrylamide.

The term "(meth)acrylate" refers to methacrylate and/or acrylate.

A "hydrophilic vinylic monomer", as used herein, refers to a vinylic monomer which can be polymerized to form a homopolymer that is water-soluble or can absorb at least 10 percent by weight of water.

A "hydrophobic vinylic monomer" refers to a vinylic monomer which can be polymerized to form a homopolymer that is insoluble in water and can absorb less than 10 percent by weight of water.

"UVA" refers to radiation occurring at wavelengths between 315 and 380 nanometers; "UVB" refers to radiation occurring between 280 and 315 nanometers; "Violet" refers to radiation occurring at wavelengths between 380 and 440 nanometers.

"UVA transmittance" (or "UVA % T"), "UVB transmittance" or "UVB % T", and "violet-transmittance" or "Violet % T" are calculated by the following formula $$UVA \% \ T = \frac{\text{Average \% Transmission between 315 and 380 nm}}{\text{Luminescence \% } T} \times 100$$

$$UVB \% \ T = \frac{\text{Average \% Transmission between 280 and 315 nm}}{\text{Luminescence \% } T} \times 100$$

$$\text{Violet \% } T = \frac{\text{Average \% Transmission between 380 and 440 nm}}{\text{Luminescence \% } T} \times 100$$

in which Luminescence % T is the luminescence percent transmittance is the ratio of luminous flux transmitted by the lens to the incident luminous flux (ISO 13666:1998).

As used in this application, the term "macromer" or "prepolymer" refers to a medium and high molecular weight compound or polymer that contains two or more ethylenically unsaturated groups. Medium and high molecular weight typically means average molecular weights greater than 700 Daltons.

As used in this application, the term "vinylic crosslinker" refers to a compound having at least two ethylenically unsaturated groups. A "vinylic crosslinking agent" refers to a vinylic crosslinker having a molecular weight of about 700 Daltons or less.

As used in this application, the term "polymer" means a material formed by polymerizing/crosslinking one or more monomers or macromers or prepolymers.

As used in this application, the term "molecular weight" of a polymeric material (including monomeric or macromeric materials) refers to the weight-average molecular weight unless otherwise specifically noted or unless testing conditions indicate otherwise.

The term "alkyl" refers to a monovalent radical obtained by removing a hydrogen atom from a linear or branched alkane compound. An alkyl group (radical) forms one bond with one other group in an organic compound.

The term "alkylene divalent group" or "alkylene diradical" or "alkyl diradical" interchangeably refers to a divalent radical obtained by removing one hydrogen atom from an alkyl. An alkylene divalent group forms two bonds with other groups in an organic compound.

The term "alkyl triradical" refers to a trivalent radical obtained by removing two hydrogen atoms from an alkyl. A alkyl triradical forms three bonds with other groups in an organic compound.

The term "alkoxy" or "alkoxyl" refers to a monovalent radical obtained by removing the hydrogen atom from the hydroxyl group of a linear or branched alkyl alcohol. An alkoxy group (radical) forms one bond with one other group in an organic compound.

In this application, the term "substituted" in reference to an alkyl diradical or an alkyl radical means that the alkyl diradical or the alkyl radical comprises at least one substituent which replaces one hydrogen atom of the alkyl diradical or the alkyl radical and is selected from the group consisting of hydroxy (—OH), carboxy (—COOH), —NH$_2$, sulfhydryl (—SH), C$_1$-C$_4$ alkyl, C$_1$-C$_4$ alkoxy, C$_1$-C$_4$ alkylthio (alkyl sulfide), C$_1$-C$_4$ acylamino, C$_1$-C$_4$ alkylamino, di-C$_1$-C$_4$ alkylamino, halogen atom (Br or Cl), and combinations thereof.

A "photoinitiator" refers to a chemical that initiates free radical crosslinking/polymerizing reaction by the use of light.

Figure 1B:
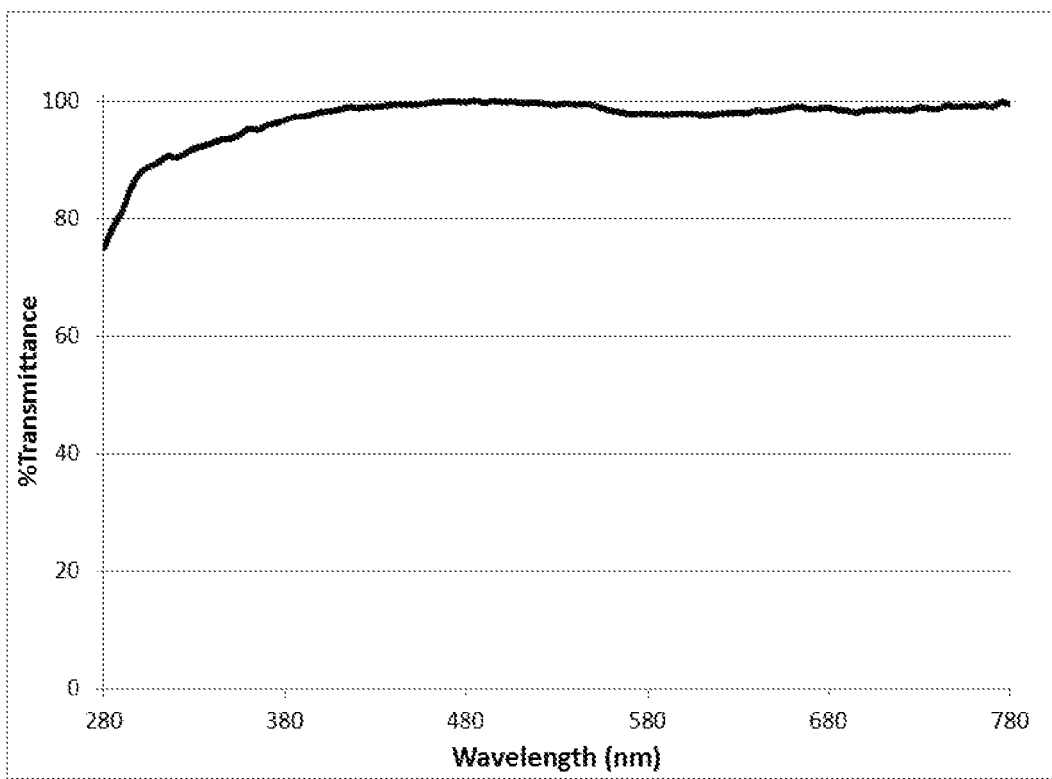
FIG. 1B shows the UV/vis spectra of a contact lens free of UV-absorbing vinylic monomer as control.

A "spatial limitation of actinic radiation" refers to an act or process in which energy radiation in the form of rays is directed by, for example, a mask or screen or combinations thereof, to impinge, in a spatially restricted manner, onto an area having a well-defined peripheral boundary. A spatial limitation of UV radiation is obtained by using a mask or screen having a radiation (e.g., UV and/or visible light) permeable region, a radiation (e.g., UV and/or visible light) impermeable region surrounding the radiation-permeable region, and a projection contour which is the boundary between the radiation-impermeable and radiation-permeable regions, as schematically illustrated in the drawings of U.S. Pat. No. 6,800,225 (FIGS. 1-11), and U.S. Pat. No. 6,627,124 (FIGS. 1-9), U.S. Pat. No. 7,384,590 (FIGS. 1-6), and U.S. Pat. No. 7,387,759 (FIGS. 1-6), all of which are incorporated by reference in their entireties. The mask or screen allows to spatially projects a beam of radiation (e.g., UV radiation and/or visible radiation) having a cross-sectional profile defined by the projection contour of the mask or screen. The projected beam of radiation (e.g., UV radiation and/or visible radiation) limits radiation impinging on a lens formulation located in the path of the projected beam from the first molding surface to the second molding surface of a mold. The resultant contact lens comprises an anterior surface defined by the first molding surface, an opposite posterior surface defined by the second molding surface, and a lens edge defined by the sectional profile of the projected UV and/or visible beam (i.e., a spatial limitation of radiation). The radiation used for the crosslinking is radiation energy, especially UV radiation (and/or visible radiation), gamma radiation, electron radiation or thermal radiation, the radiation energy preferably being in the form of a substantially parallel beam in order on the one hand to achieve good restriction and on the other hand efficient use of the energy.

The term "modulus" or "elastic modulus" in reference to a contact lens or a material means the tensile modulus or Young's modulus which is a measure of the stiffness of a contact lens or a material. The modulus can be measured using a method in accordance with ANSI Z80.20 standard. A person skilled in the art knows well how to determine the elastic modulus of a silicone hydrogel material or a contact lens. For example, all commercial contact lenses have reported values of elastic modulus.

In general, the invention is directed to a class of amino benzophenone vinylic monomer which absorbs between 380 and 460 nm, shows good solubility in formulations, is photo-stable, and is inexpensive to make. An amino benzophenone vinylic monomer of the invention is suitable for making UV-absorbing hydrogel contact lenses capable of absorbing a light between 380 and 460 nm.

In one aspect, the present invention provides a UV-absorbing vinylic monomer of formula (I)

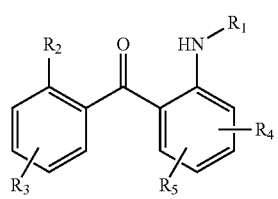

(I)

in which:
- $R_1$ is hydrogen, a (meth)acryloyl group, or a radical of $-L_1-Q_1$ in which $L_1$ is a $C_2$-$C_4$ alkylene divalent radical and $Q_1$ is a (meth)acryloyloxy group;
- $R_2$ is hydrogen, $CH_3$, $CCl_3$, $CF_3$, F, Cl, Br, OH, $OCH_3$, COOH, $NH_2$, a radical of —CO—NH-$L_1$-$Q_2$ in which $L_1$ is a $C_2$-$C_4$ alkylene divalent radical and $Q_2$ is a (meth)acryloyloxy or (meth)acryloylamido group; and
- $R_3$, $R_4$, and $R_5$ independent of one other are H, $CH_3$, $CCl_3$, $CF_3$, F, Cl, Br, $NO_2$, OH, $OCH_3$, or NR'R" in which R' and R" independent of each other are H or $C_1$-$C_4$ alkyl;

provided that only one of $R_1$ and $R_2$ contains a (meth)acryloylamido or (meth)acryloyloxy group.

Examples of preferred UV-absorbing vinylic monomer of formula (I) include without limitation:

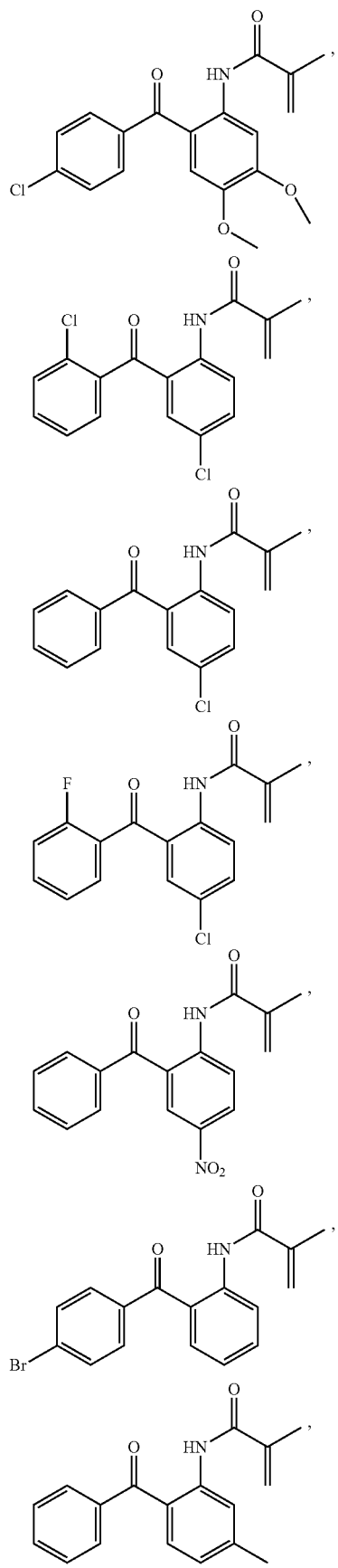

-continued
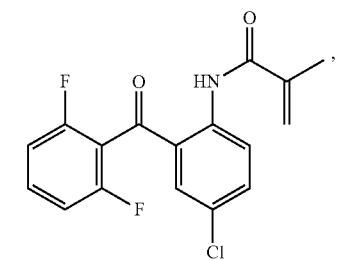
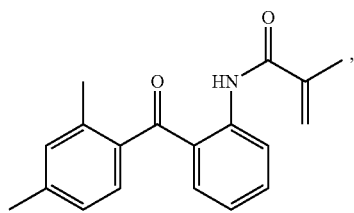
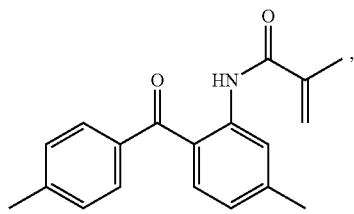
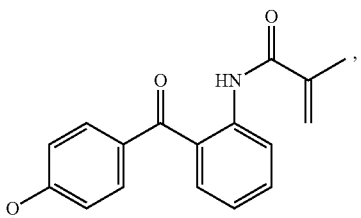
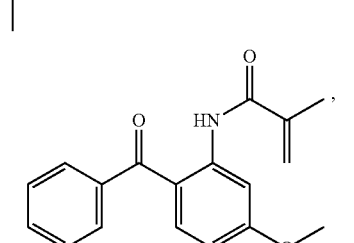
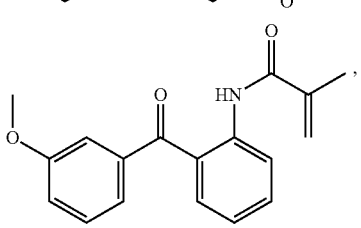
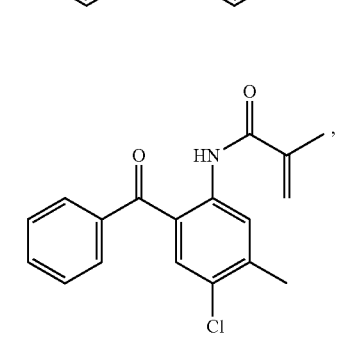
-continued
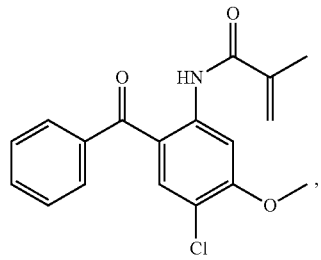
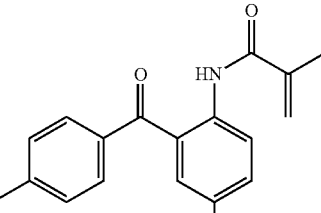
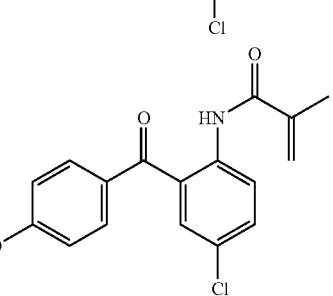
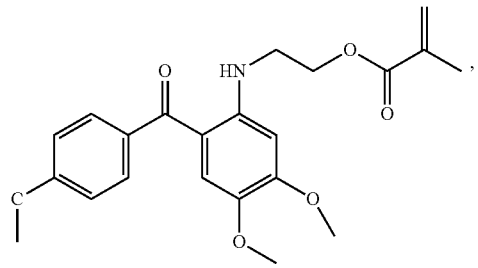
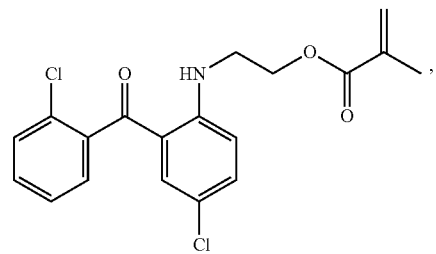
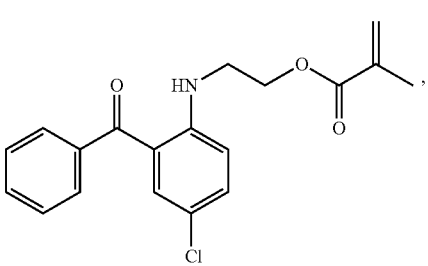

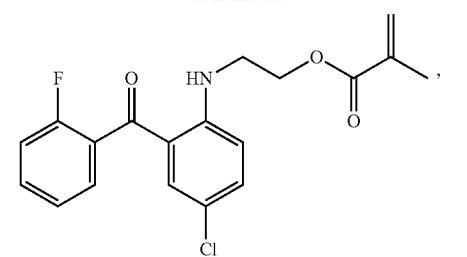
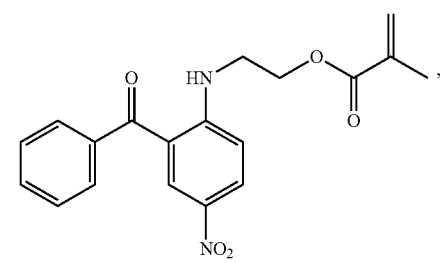
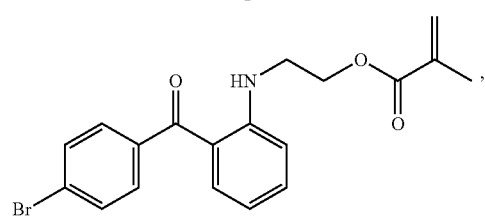
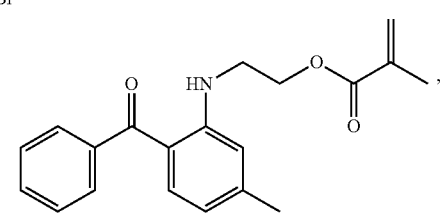
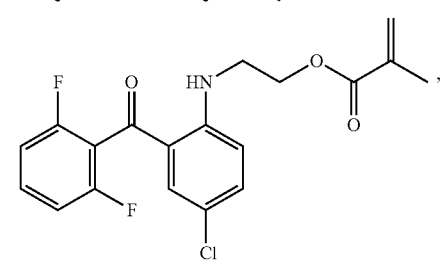
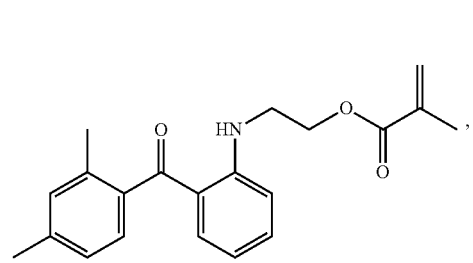
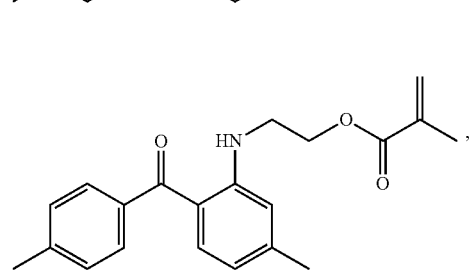
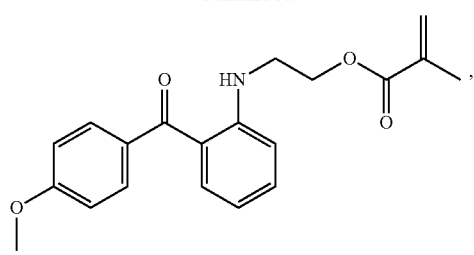
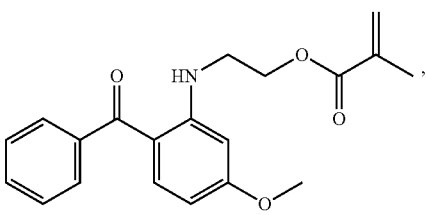
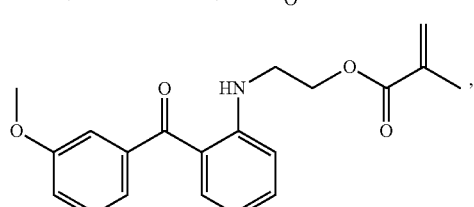
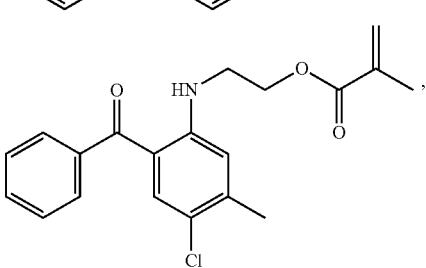
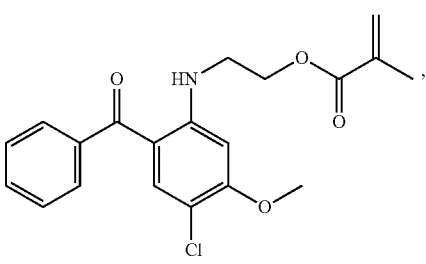
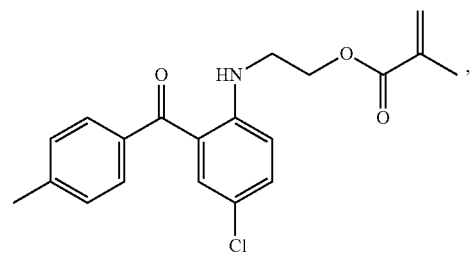
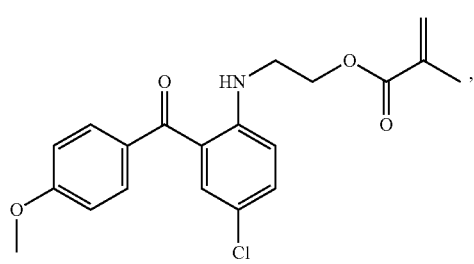

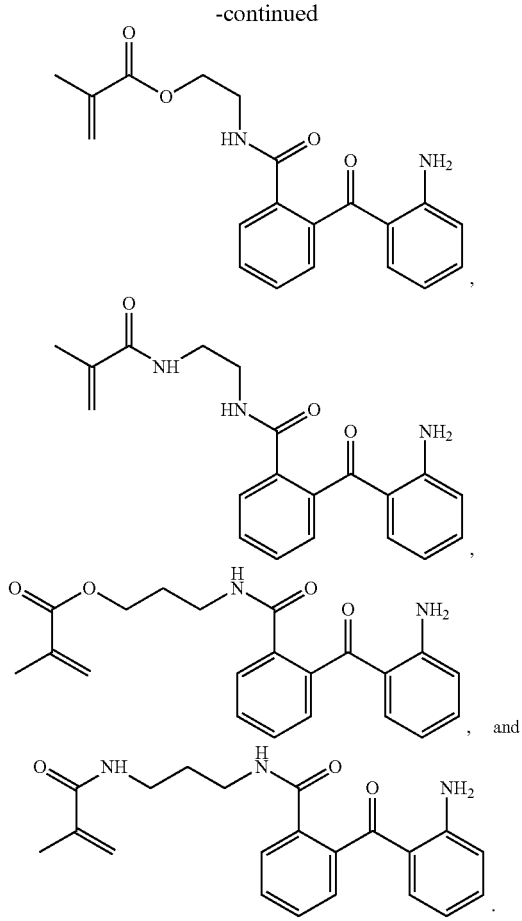

An UV-absorbing vinylic monomer of formula (I) can be prepared from commercially available 2-aminobenzophenones with various substituents. Examples of such 2-aminobenzophenones with various substituents include with limitation 2-amino-5-chlorobenzophenone, 2-amino-5-chloro-2'-fluorobenzophenone, 2-amino-2',5-dichlorobenzophenone, 2-amino-5-nitrobenzophenone, 2-amino-4'-bromobenzophenone, 2-amino-4-methylbenzophenone, 2-amino-5-chloro-2',6'-diflorobenzophenone, 2-amino-2',4'-dimethylbenzophnenone, 2-amino-4,4'-dimethylbenzophenone, 2-amino-4'-methoxybenzophenone, 2-amino-4-methoxybenzophenone, 2-amino-3'-methoxybenzophenone, 2-amino-5-chloro-4-methylbenzophenone, 2-amino-5-chloro-4'methoxybenzophenone, 2-amino-5-chloro-4'-methyl benzophenone, 2-amino-5-chloro-4'-methoxybenzophenone, and 2-amino-benzopheonone-2'carboxylic acid. Examples of synthetic procedures for their preparations are illustrated in Schemes 1 to 3.

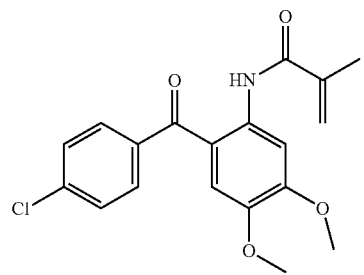

Scheme 2

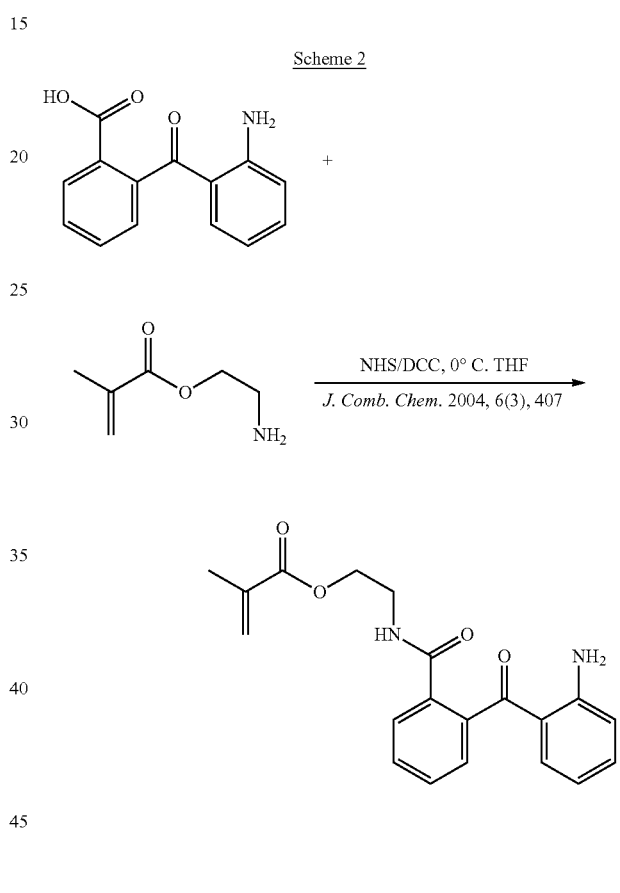

Scheme 3

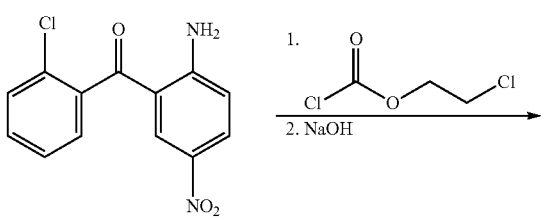

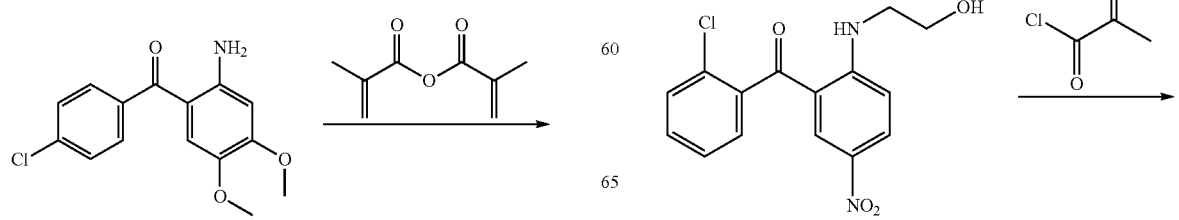

-continued

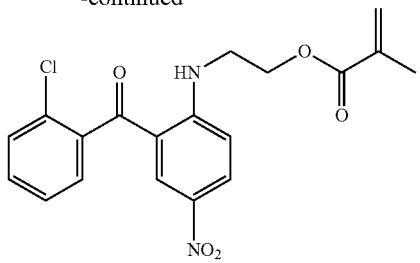

ref: *Chem. Pharm. Bull*, 1979, 27(4), 880

An UV-absorbing vinylic monomer of formula (I) can find particular use for making hydrogel contact lenses.

In another aspect, the invention provides a method for producing UV-absorbing contact lenses, comprising the steps of: (1) obtaining a lens formulation comprising (a) a UV-absorbing vinylic monomer of formula (I) (as defined above), (b) a free-radical initiator, and (c) at least one polymerizable component selected from the group consisting of a hydrophilic vinylic monomer, a hydrophobic vinylic monomer free of silicone, a vinylic crosslinking agent, a siloxane-containing vinylic monomer, a siloxane containing vinylic macromer, a water-soluble prepolymer free of silicone, and a siloxane-containing amphiphilic prepolymer; (2) introducing the lens formulation into a mold for making a soft contact lens, wherein the mold has a first mold half with a first molding surface defining the anterior surface of a contact lens and a second mold half with a second molding surface defining the posterior surface of the contact lens, wherein said first and second mold halves are configured to receive each other such that a cavity is formed between said first and second molding surfaces; and (3) curing thermally or actinically the lens formulation in the mold to crosslink the UV-absorbing vinylic monomer and the polymerizable component in the lens formulation to form the UV-absorbing contact lens, wherein the formed UV-absorbing contact lens comprises an anterior surface defined by the first molding surface and an opposite posterior surface defined by the second molding surface and is characterized by having the UVB transmittance of about 10% or less (preferably about 5% or less, more preferably about 2.5% or less, even more preferably about 1% or less) between 280 and 315 nanometers and a UVA transmittance of about 30% or less (preferably about 20% or less, more preferably about 10% or less, even more preferably about 5% or less) between 315 and 380 nanometers and and optionally (but preferably) a Violet transmittance of about 60% or less, preferably about 50% or less, more preferably about 40% or less, even more preferably about 30% or less) between 380 nm and 440 nm.

It is understood that the amount of UV-absorbing units present in the prepolymer in the aqueous lens formulation is sufficient to render a resultant contact lens, which is obtained from the curing of the lens formulation, ability of blocking or absorbing (i.e., the inverse of transmittance) at least 90% (preferably at least about 95%, more preferably at least about 97.5%, even more preferably at least about 99%) of UVB (between 280 and 315 nanometers), at least 70% (preferably at least about 80%, more preferably at least about 90%, even more preferably at least about 95%) of UVA transmittance (between 315 and 380 nanometers), and optionally (but preferably) at least 30% (preferably at least about 40%, more preferably at least about 50%, even more preferably at least about 60%) of violet light between 380 nm and 440 nm, which impinge on the lens.

In accordance with the invention, any thermal free-radical initiators can be used in the invention. Examples of suitable thermal initiators include, but are not limited to, 2,2'-azobis (2,4-dimethylpentanenitrile), 2,2'-azobis (2-methylpropanenitrile), 2,2'-azobis (2-methylbutanenitrile), peroxides such as benzoyl peroxide, and the like. Preferably, the thermal initiator is 2,2'-azobis(isobutyronitrile) (AIBN).

Suitable photoinitiators are benzoin methyl ether, diethoxyacetophenone, a benzoylphosphine oxide, 1-hydroxycyclohexyl phenyl ketone and Darocur and Irgacur types, preferably Darocur 1173® and Darocur 2959®, Germanium-based Norrish Type I photoinitiators. Examples of benzoylphosphine initiators include 2,4,6-trimethylbenzoyl-diphenylophosphine oxide; bis-(2,6-dichlorobenzoyl)-4-N-propylphenylphosphine oxide; and bis-(2,6-dichlorobenzoyl)-4-N-butylphenylphosphine oxide. Reactive photoinitiators which can be incorporated, for example, into a macromer or can be used as a special monomer are also suitable. Examples of reactive photoinitiators are those disclosed in EP 632 329, herein incorporated by reference in its entirety. Examples of Germanium-based Norrish Type I photoinitiators are acylgermanium compounds described in U.S. Pat. No. 7,605,190 (herein incorporated by reference in its entirety) and water-soluble Germanium-based Norrish Type I photoinitiators disclosed in U.S. Pat. Appl. No. 62/169,722 (herein incorporated by reference in its entirety). The polymerization can then be triggered off by actinic radiation, for example light, in particular UV/visible light of a suitable wavelength. The spectral requirements can be controlled accordingly, if appropriate, by addition of suitable photosensitizers.

Polymerizable components for making contact lenses are well known to a person skilled in the art, including, for example, such as, vinylic monomers, vinylic macromers, prepolymers, vinylic crosslinking agents, or combinations thereof, as known to a person skilled in the art. A lens formulation can further include other components, such as a visibility tinting agent, antimicrobial agents (e.g., Ag-nanoparticles), lubricant/wetting agents, and the like.

Nearly any hydrophilic vinylic monomer can be used in the invention. Suitable hydrophilic vinylic monomers are, without this being an exhaustive list, N,N-dimethylacrylamide (DMA), N,N-dimethyl methacrylamide (DMMA), 2-acrylamidoglycolic acid, N-hydroxypropyl acrylamide, N-hydroxyethyl acrylamide, N-hydroxypropyl methacrylamide, N-hydroxyethyl methacrylamide, N-[tris(hydroxymethyl)methyl]-acrylamide, N-vinylpyrrolidone (NVP), N-vinyl formamide, N-vinyl acetamide, N-vinyl isopropylamide, N-vinyl-N-methyl acetamide (VMA), N-methyl-3-methylene-2-pyrrolidone, 1-methyl-5-methylene-2-pyrrolidone, 5-methyl-3-methylene-2-pyrrolidone, 2-hydroxyethylmethacrylate (HEMA), 2-hydroxyethyl acrylate (HEA), hydroxypropyl acrylate, hydroxypropyl methacrylate, methoxyethylmethacrylate (i.e., ethylene glycol methyl ether methacrylate, EGMA), trimethylammonium 2-hydroxy propylmethacrylate hydrochloride, aminopropyl methacrylate hydrochloride, dimethylaminoethyl methacrylate (DMAEMA), glycerol methacrylate (GMA), a $C_1$-$C_4$-alkoxy polyethylene glycol (meth)acrylate having a weight average molecular weight of up to 1500, polyethylene glycol (meth)acrylate having a weight average molecular weight of up to 1500, methacrylic acid, acrylic acid, and mixtures thereof.

Nearly any non-silicone hydrophobic vinylic monomer can be used. Examples of preferred non-silicone hydrophobic vinylic monomers include methylacrylate, ethyl-acrylate, propylacrylate, isopropylacrylate, cyclohexylacrylate, 2-ethylhexylacrylate, methylmethacrylate, ethyl methacrylate, propylmethacrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyl toluene, vinyl ethyl ether, perfluorohexylethyl-thio-carbonyl-aminoethyl-methacrylate, isobornyl methacrylate, trifluoroethyl methacrylate, hexafluoro-isopropyl methacrylate, hexafluorobutyl methacrylate. By incorporating a certain amount of non-silicone hydrophobic vinylic monomer in a lens formulation, the mechanical properties (e.g., modulus of elasticity) of the resultant polymer may be improved.

Examples of preferred vinylic crosslinking agents include without limitation tetraethyleneglycol di(meth)acrylate, triethyleneglycol di(meth)acrylate, diethyleneglycol di(meth) acrylate, ethyleneglycol di(meth)acrylate, tetraethyleneglycol divinyl ether, triethyleneglycol divinyl ether, diethyleneglycol divinyl ether, ethyleneglycol divinyl ether, trimethylopropane tri methacrylate, pentaerythritol tetramethacrylate, bisphenol A dimethacrylate, vinyl methacrylate, ethylenediamine di(meth)acrylamide, glycerol di(meth) acrylate, triallyl isocyanurate, triallyl cyanurate, allyl(meth) acrylate, N-allyl-(meth)acrylamide, 1,3-bis(methacrylamidopropyl)-1,1,3,3-tetrakis(trimethylsiloxy)disiloxane, N,N'-methylenebisacrylamide, N,N'-methylenebismethacrylamide, N,N'-ethylenebisacrylamide, N,N'-ethylenebismethacrylamide,1,3-bis(N-methacrylamidopropyl)-1,1,3,3-tetrakis-(trimethylsiloxy)disiloxane, 1,3-bis(methacrylamidobutyl)-1,1,3,3-tetrakis(trimethylsiloxy)-disiloxane, 1,3-bis(acrylamidopropyl)-1,1,3,3-tetrakis(trimethylsiloxy)disiloxane, 1,3-bis(methacryloxyethylureidopropyl)-1,1,3,3-tetrakis(trimethylsiloxy)disiloxane, and combinations thereof. The amount of a cross-linking agent used is expressed in the weight content with respect to the total polymer and is preferably in the range from about 0.05% to about 3%, and more preferably in the range from about 0.1% to about 2%.

Any suitable siloxane-containing vinylic monomers can be used in the invention. Examples of preferred siloxane-containing vinylic monomers include without limitation N-[tris(trimethylsiloxy)silylpropyl]-(meth)acrylamide, N-[tris(dimethylpropylsiloxy)-silylpropyl]-(meth)acrylamide, N-[tris(dimethylphenylsiloxy)silylpropyl] (meth)acrylamide, N-[tris(dimethylethylsiloxy)silylpropyl] (meth)acrylamide, N-(2-hydroxy-3-(3-(bis(trimethylsilyloxy)-methylsilyl)propyloxy)propyl)-2-methyl acrylamide; N-(2-hydroxy-3-(3-(bis(trimethylsilyloxy)-methylsilyl)propyloxy)propyl) acrylamide; N,N-bis[2-hydroxy-3-(3-(bis(trimethylsilyloxy)-methylsilyl)propyloxy)propyl]-2-methyl acrylamide; N, N-bis[2-hydroxy-3-(3-(bis(trimethylsilyloxy)-methylsilyl)propyloxy) propyl] acrylamide; N-(2-hydroxy-3-(3-(tris(trimethylsilyloxy)silyl)-propyloxy)propyl)-2-methyl acrylamide; N-(2-hydroxy-3-(3-(tris(trimethylsilyloxy)silyl)propyloxy)-propyl) acrylamide; N,N-bis[2-hydroxy-3-(3-(tris(trimethylsilyloxy)silyl)propyloxy)propyl]-2-methyl acrylamide; N,N-bis[2-hydroxy-3-(3-(tris(trimethylsilyloxy)silyl)propyloxy)propyl]acrylamide; N-[2-hydroxy-3-(3-(t-butyldimethylsilyl) propyloxy)propyl]-2-methyl acrylamide; N-[2-hydroxy-3-(3-(t-butyldimethylsilyl)propyloxy) propyl]acrylamide; N,N-bis[2-hydroxy-3-(3-(t-butyldimethylsilyl)-propyloxy)propyl]-2-methyl acrylamide; N,N-bis[2-hydroxy-3-(3-(t-butyldimethylsilyl) propyloxy)-propyl]acrylamide; 3-methacryloxy propylpentamethyldisiloxane, tris(trimethylsilyloxy)silylpropyl methacrylate (TRIS), (3-methacryloxy-2-hydroxypropyloxy) propylbis(trimethylsiloxy)-methylsilane), (3-methacryloxy-2-hydroxypropyloxy)propyltris(trimethylsiloxy)silane, 3-methacryloxy-2-(2-hydroxyethoxy)-propyloxy)propylbis(trimethylsiloxy)methylsilane, N-2-methacryloxyethyl-O-(methyl-bis-trimethylsiloxy-3-propyl)silylcarbamate, 3-(trimethylsilyl)-propylvinyl carbonate, 3-(vinyloxycarbonylthio)propyl-tris(trimethyl-siloxy)silane, 3-[tris(trimethyl-siloxy)silyl]propylvinyl carbamate, 3-[tris(trimethylsiloxy)silyl] propyl allyl carbamate, 3-[tris(trimethylsiloxy) silyl]propyl vinyl carbonate, t-butyldimethyl-siloxyethyl vinyl carbonate; trimethylsilylethyl vinyl carbonate, and trimethylsilylmethyl vinyl carbonate); monomethacrylated or monoacrylated polydimethylsiloxanes of various molecular weight (e.g., mono-3-methacryloxypropyl terminated, mono-butyl terminated polydimethylsiloxane or mono-(3-methacryloxy-2-hydroxypropyloxy)propyl terminated, mono-butyl terminated polydimethylsiloxane); mono-vinyl carbonate-terminated polydimethylsiloxanes; mono-vinyl carbamate-terminated polydimethylsiloxane; mono-methacrylamide-terminated polydimethylsiloxanes; mono-acrylamide-terminated polydimethylsiloxanes; carbosiloxane vinylic monomers disclosed in U.S. Pat. Nos. 7,915,323 and 8,420,711, in US Patent Applicaton Publication Nos. 2012/244088 and 2012/245249 (herein incorporated by references in their entireties); combinations thereof.

Any suitable siloxane-containing vinylic macromers (or crosslinkers) can be used in the invention. Examples of preferred siloxane-containing vinylic macromers are dimethacrylated or diacrylated polydimethylsiloxanes of various molecular weight; di-vinyl carbonate-terminated polydimethylsiloxanes; di-vinyl carbamate-terminated polydimethylsiloxane; di-methacrylamide-terminated polydimethylsiloxanes; di-acrylamide-terminated polydimethylsiloxanes; bis-3-methacryloxy-2-hydroxypropyloxypropyl polydimethylsiloxane; N,N,N',N'-tetrakis(3-methacryloxy-2-hydroxypropyl)-alpha,omega-bis-3-aminopropyl-polydimethylsiloxane; polysiloxanylalkyl (meth)acrylic monomers; siloxane-containing macromer selected from the group consisting of Macromer A, Macromer B, Macromer C, and Macromer D described in U.S. Pat. No. 5,760,100 (herein incorporated by reference in its entirety); chain-extended polysiloxane vinylic crosslinkers disclosed in US201008843A1 and US20120088844A1 (herein incorporated by references in their entireties); the reaction products of glycidyl methacrylate with amino-functional polydimethylsiloxanes; hydroxyl-functionalized siloxane-containing vinylic monomers or macromers; polysiloxane-containing macromers disclosed in U.S. Pat. Nos. 4,136,250, 4,153, 641, 4,182,822, 4,189,546, 4,343,927, 4,254,248, 4,355,147, 4,276,402, 4,327,203, 4,341,889, 4,486,577, 4,543,398, 4,605,712, 4,661,575, 4,684,538, 4,703,097, 4,833,218, 4,837,289, 4,954,586, 4,954,587, 5,010,141, 5,034,461, 5,070,170, 5,079,319, 5,039,761, 5,346,946, 5,358,995, 5,387,632, 5,416,132, 5,451,617, 5,486,579, 5,962,548, 5,981,675, 6,039,913, and 6,762,264 (here incorporated by reference in their entireties); polysiloxane-containing macromers disclosed in U.S. Pat. Nos. 4,259,467, 4,260,725, and 4,261,875 (herein incorporated by reference in their entireties).

Examples of water-soluble prepolymers (free of silicone) include without limitation: a water-soluble crosslinkable poly(vinyl alcohol) prepolymer described in U.S. Pat. Nos. 5,583,163 and 6,303,687; a water-soluble vinyl group-terminated polyurethane prepolymer described in U.S. Pat. No. 6,995,192; derivatives of a polyvinyl alcohol, polyethyleneimine or polyvinylamine, which are disclosed in U.S. Pat. No. 5,849,841; a water-soluble crosslinkable polyurea prepolymer described in U.S. Pat. Nos. 6,479,587 and 7,977,430; crosslinkable polyacrylamide; crosslinkable statistical copolymers of vinyl lactam, MMA and a comonomer, which are disclosed in U.S. Pat. No. 5,712,356; crosslinkable copolymers of vinyl lactam, vinyl acetate and vinyl alcohol, which are disclosed in U.S. Pat. No. 5,665,840; polyether-polyester copolymers with crosslinkable side chains which are disclosed in U.S. Pat. No. 6,492,478; branched polyalkylene glycol-urethane prepolymers disclosed in U.S. Pat. No. 6,165,408; polyalkylene glycol-tetra (meth)acrylate prepolymers disclosed in U.S. Pat. No. 6,221, 303; crosslinkable polyallylamine gluconolactone prepolymers disclosed in U.S. Pat. No. 6,472,489; all of which are incorporated herein by references in their entireties.

Any suitable of silicone-containing prepolymers with hydrophilic segments and hydrophobic segments can be used in the invention. Examples of such silicone-containing prepolymers include those described in commonly-owned U.S. Pat. Nos. 6,039,913, 7,091,283, 7,268,189 and 7,238, 750, 7,521,519; commonly-owned US patent application publication Nos. US 2008-0015315 A1, US 2008-0143958 A1, US 2008-0143003 A1, US 2008-0234457 A1, US 2008-0231798 A1, and commonly-owned US patent application Nos. 61/180,449 and 61/180,453; all of which are incorporated herein by references in their entireties.

A lens formulation of the invention can further comprise visibility tinting agents (e.g., D&C Blue No. 6, D&C Green No. 6, D&C Violet No. 2, carbazole violet, certain copper complexes, certain chromium oxides, various iron oxides, phthalocyanine green, phthalocyanine blue, titanium dioxides, or mixtures thereof), antimicrobial agents (e.g., silver nanoparticles), a bioactive agent (e.g., a drug, an amino acid, a polypeptide, a protein, a nucleic acid, 2-pyrrolidone-5-carboxylic acid (PCA), an alpha hydroxyl acid, linoleic and gamma linoleic acids, vitamins, or any combination thereof), leachable lubricants (e.g., a non-crosslinkable hydrophilic polymer having an average molecular weight from 5,000 to 500,000, preferably from 10,000 to 300,000, more preferably from 20,000 to 100,000 Daltons), leachable tear-stabilizing agents (e.g., a phospholipid, a monoglyceride, a diglyceride, a triglyceride, a glycolipid, a glyceroglycolipid, a sphingolipid, a sphingo-glycolipid, a fatty acid having 8 to 36 carbon atoms, a fatty alcohol having 8 to 36 carbon atoms, or a mixture thereof), and the like, as known to a person skilled in the art.

In accordance with the invention, a lens formulation is preferably a solution of all desirable components dissolved in a suitable solvent (i.e., one chemical that cannot participate in free-radical polymerization reaction) or a mixture of suitable solvents or a liquid mixture free of any organic solvent.

A lens formulation can be prepared by blending all components thoroughly or by dissolving all of the desirable components in any suitable solvent, such as, a mixture of water and one or more organic solvents miscible with water, an organic solvent, or a mixture of one or more organic solvents, as known to a person skilled in the art.

Example of preferred organic solvents includes without limitation, tetrahydrofuran, tripropylene glycol methyl ether, dipropylene glycol methyl ether, ethylene glycol n-butyl ether, ketones (e.g., acetone, methyl ethyl ketone, etc.), diethylene glycol n-butyl ether, diethylene glycol methyl ether, ethylene glycol phenyl ether, propylene glycol methyl ether, propylene glycol methyl ether acetate, dipropylene glycol methyl ether acetate, propylene glycol n-propyl ether, dipropylene glycol n-propyl ether, tripropylene glycol n-butyl ether, propylene glycol n-butyl ether, dipropylene glycol n-butyl ether, tripropylene glycol n-butyl ether, propylene glycol phenyl ether dipropylene glycol dimetyl ether, polyethylene glycols, polypropylene glycols, ethyl acetate, butyl acetate, amyl acetate, methyl lactate, ethyl lactate, i-propyl lactate, methylene chloride, 2-butanol, 1-propanol, 2-propanol, menthol, cyclohexanol, cyclopentanol and exonorborneol, 2-pentanol, 3-pentanol, 2-hexanol, 3-hexanol, 3-methyl-2-butanol, 2-heptanol, 2-octanol, 2-nonanol, 2-decanol, 3-octanol, norborneol, tert-butanol, tert-amyl alcohol, 2-methyl-2-pentanol, 2,3-dimethyl-2-butanol, 3-methyl-3-pentanol, 1-methylcyclohexanol, 2-methyl-2-hexanol, 3,7-dimethyl-3-octanol, 1-chloro-2-methyl-2-propanol, 2-methyl-2-heptanol, 2-methyl-2-octanol, 2-2-methyl-2-nonanol, 2-methyl-2-decanol, 3-methyl-3-hexanol, 3-methyl-3-heptanol, 4-methyl-4-heptanol, 3-methyl-3-octanol, 4-methyl-4-octanol, 3-methyl-3-nonanol, 4-methyl-4-nonanol, 3-methyl-3-octanol, 3-ethyl-3-hexanol, 3-methyl-3-heptanol, 4-ethyl-4-heptanol, 4-propyl-4-heptanol, 4-isopropyl-4-heptanol, 2,4-dimethyl-2-pentanol, 1-methylcyclopentanol, 1-ethylcyclopentanol, 1-ethylcyclopentanol, 3-hydroxy-3-methyl-1-butene, 4-hydroxy-4-methyl-1-cyclopentanol, 2-phenyl-2-propanol, 2-methoxy-2-methyl-2-propanol 2,3,4-trimethyl-3-pentanol, 3,7-dimethyl-3-octanol, 2-phenyl-2-butanol, 2-methyl-1-phenyl-2-propanol and 3-ethyl-3-pentanol, 1-ethoxy-2-propanol, 1-methyl-2-propanol, t-amyl alcohol, isopropanol, 1-methyl-2-pyrrolidone, N,N-dimethylpropionamide, dimethyl formamide, dimethyl acetamide, dimethyl propionamide, N-methyl pyrrolidinone, and mixtures thereof.

Lens molds for making contact lenses are well known to a person skilled in the art and, for example, are employed in cast molding or spin casting. For example, a mold (for cast molding) generally comprises at least two mold sections (or portions) or mold halves, i.e. first and second mold halves. The first mold half defines a first molding (or optical) surface and the second mold half defines a second molding (or optical) surface. The first and second mold halves are configured to receive each other such that a lens forming cavity is formed between the first molding surface and the second molding surface. The molding surface of a mold half is the cavity-forming surface of the mold and in direct contact with lens-forming material.

Methods of manufacturing mold sections for cast-molding a contact lens are generally well known to those of ordinary skill in the art. The process of the present invention is not limited to any particular method of forming a mold. In fact, any method of forming a mold can be used in the present invention. The first and second mold halves can be formed through various techniques, such as injection molding or lathing. Examples of suitable processes for forming the mold halves are disclosed in U.S. Pat. No. 4,444,711 to Schad; U.S. Pat. No. 4,460,534 to Boehm et al.; U.S. Pat. No. 5,843,346 to Morrill; and U.S. Pat. No. 5,894,002 to Boneberger et al., which are also incorporated herein by reference.

Virtually all materials known in the art for making molds can be used to make molds for making contact lenses. For example, polymeric materials, such as polyethylene, polypropylene, polystyrene, PMMA, Topas® COC grade 8007-S10 (clear amorphous copolymer of ethylene and norbornene, from Ticona GmbH of Frankfurt, Germany and Summit, N.J.), or the like can be used. Other materials that allow UV light transmission could be used, such as quartz glass and sapphire.

In a preferred embodiment, reusable molds are used and the silicone-hydrogel lens-forming composition is cured actinically under a spatial limitation of actinic radiation to form a SiHy contact lens. Examples of preferred reusable molds are those disclosed in U.S. patent application Ser. No. 08/274,942 filed Jul. 14, 1994, Ser. No. 10/732,566 filed Dec. 10, 2003, Ser. No. 10/721,913 filed Nov. 25, 2003, and U.S. Pat. No. 6,627,124, which are incorporated by reference in their entireties. Reusable molds can be made of quartz, glass, sapphire, $CaF_2$, a cyclic olefin copolymer (such as for example, Topas® COC grade 8007-S10 (clear amorphous copolymer of ethylene and norbornene) from Ticona GmbH of Frankfurt, Germany and Summit, N.J., Zeonex® and Zeonor® from Zeon Chemicals LP, Louisville, Ky.), polymethylmethacrylate (PMMA), polyoxymethylene from DuPont (Delrin), Ultem® (polyetherimide) from G.E. Plastics, PrimoSpire®, etc.

In accordance with the invention, the lens formulation can be introduced (dispensed) into a cavity formed by a mold according to any known methods.

After the lens formulation is dispensed into the mold, it is cured (i.e., polymerized) to produce a contact lens. Curing may be initiated thermally or upon exposure to a light source including a light in a region between 390 nm to 500 nm to crosslink the polymerizable components in the lens formulation.

In accordance with the invention, light source can be any ones emitting light in the 390-500 nm range sufficient to activate photoinitiators. Blue-light sources are commercially available and include: the Palatray CU blue-light unit (available from Heraeus Kulzer, Inc., Irvine, Calif.), the Fusion F450 blue light system (available from TEAMCO, Richardson, Tex.), Dymax Blue Wave 200, LED light sources from Opsytec (385 nm, 395 nm, 405 nm, 435 nm, 445 nm, 460 nm), LED light sources from Hamamatsu (385 nm), and the GE 24" blue fluorescent lamp (available from General Electric Company, U.S.). A preferred blue-light source is the UV LED from Opsytec (those described above).

Opening of the mold so that the molded lens can be removed from the mold may take place in a manner known per se.

The molded contact lens can be subjected to one or more post-molding processes, such as, for example, lens extraction to remove unpolymerized vinylic monomers and macromers, surface modification to improve the surface hydrophilicity and wettability of a molded lens, hydration, packaging, sterilization (e.g., autoclave), as known to a person skilled in the art.

Lens packages (or containers) are well known to a person skilled in the art for autoclaving and storing a soft contact lens. Any lens packages can be used in the invention. Preferably, a lens package is a blister package which comprises a base and a cover, wherein the cover is detachably sealed to the base, wherein the base includes a cavity for receiving a sterile packaging solution and the contact lens.

Lenses are packaged in individual packages, sealed, and sterilized (e.g., by autoclave at about 120° C. or higher for at least 30 minutes under pressure) prior to dispensing to users. A person skilled in the art will understand well how to seal and sterilize lens packages.

In accordance with the invention, a packaging solution contains at least one buffering agent and one or more other ingredients known to a person skilled in the art. Examples of other ingredients include without limitation, tonicity agents, surfactants, antibacterial agents, preservatives, and lubricants (e.g., cellulose derivatives, polyvinyl alcohol, polyvinyl pyrrolidone).

The packaging solution contains a buffering agent in an amount sufficient to maintain a pH of the packaging solution in the desired range, for example, preferably in a physiologically acceptable range of about 6.5 to about 7.5. Any known, physiologically compatible buffering agents can be used. Suitable buffering agents as a constituent of the contact lens care composition according to the invention are known to the person skilled in the art. Examples are boric acid, borates, e.g. sodium borate, citric acid, citrates, e.g. potassium citrate, bicarbonates, e.g. sodium bicarbonate, TRIS (2-amino-2-hydroxymethyl-1,3-propanediol), Bis-Tris (Bis-(2-hydroxyethyl)-imino-tris-(hydroxymethyl)-methane), bis-aminopolyols, triethanolamine, ACES (N-(2-hydroxyethyl)-2-aminoethanesulfonic acid), BES (N,N-Bis(2-hydroxyethyl)-2-aminoethanesulfonic acid), HEPES (4-(2-hydroxyethyl)-1-piperazineethanesulfonic acid), MES (2-(N-morpholino)ethanesulfonic acid), MOPS (3-[N-morpholino]-propanesulfonic acid), PIPES (piperazine-N, N'-bis(2-ethanesulfonic acid), TES (N-[Tris (hydroxymethyl)methyl]-2-am inoethanesulfonic acid), salts thereof, phosphate buffers, e.g. $Na_2HPO_4$, $NaH_2PO_4$, and $KH_2PO_4$ or mixtures thereof. A preferred bis-aminopolyol is 1,3-bis(tris[hydroxymethyl]-methylamino)propane (bis-TRIS-propane). The amount of each buffer agent in a packaging solution is preferably from 0.001% to 2%, preferably from 0.01% to 1%; most preferably from about 0.05% to about 0.30% by weight.

The packaging solution has a tonicity of from about 200 to about 450 milliosmol (mOsm), preferably from about 250 to about 350 mOsm. The tonicity of a packaging solution can be adjusted by adding organic or inorganic substances which affect the tonicity. Suitable occularly acceptable tonicity agents include, but are not limited to sodium chloride, potassium chloride, glycerol, propylene glycol, polyols, mannitols, sorbitol, xylitol and mixtures thereof.

A packaging solution of the invention has a viscosity of from about 1 centipoise to about 8 centipoises, more preferably from about 1.5 centipoises to about 5 centipoises, at 25° C.

In still a further aspect, the invention provides a contact lens comprising a crosslinked polymeric material.

A contact lens of the invention preferably is characterized by having an UVB transmittance of about 10% or less (preferably about 5% or less, more preferably about 2.5% or less, even more preferably about 1% or less) between 280 and 315 nanometers and a UVA transmittance of about 30% or less (preferably about 20% or less, more preferably about 10% or less, even more preferably about 5% or less) between 315 and 380 nanometers and optionally (but preferably) a Violet transmittance of about 60% or less, preferably about 50% or less, more preferably about 40% or less, even more preferably about 30% or less) between 380 nm and 440 nm.

In a preferred embodiment, a contact lens of the invention is a non-silicone hydrogel contact lens which has a water content of preferably from about 15% to about 80%, more preferably from about 30% to about 70% by weight (at room temperature, about 22° C. to 28° C.) when fully hydrated.

In another preferred embodiment, a contact lens of the invention is a silicone hydrogel contact lens. It preferably has one property selected from the group consisting of: an oxygen permeability of at least about 40 barrers, preferably at least about 50 barrers, more preferably at least about 60 barrers, even more preferably at least about 70 barrers; an elastic modulus of about 1.5 MPa or less, preferably about 1.2 MPa or less, more preferably about 1.0 MPa or less, even more preferably from about 0.2 MPa to about 1.0 MPa; a water content of from about 15% to about 70%, preferably from about 20% to about 65%, more preferably from about 25% to about 60%, even more preferably from about 30% to about 55% by weight when fully hydrated; and combinations thereof.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part or can be combined in any manner and/or used together, as illustrated below:

1. A UV-absorbing vinylic monomer of formula (I)

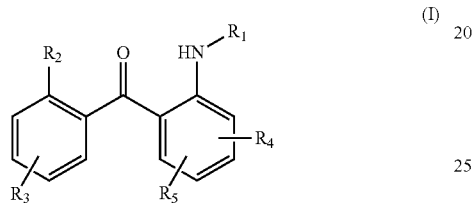

in which:

R$_1$ is hydrogen, a (meth)acryloyl group, or a radical of -L$_1$-Q$_1$ in which L$_1$ is a C$_2$-C$_4$ alkylene divalent radical and Q$_1$ is a (meth)acryloyloxy group;

R$_2$ is hydrogen, CH$_3$, CCl$_3$, CF$_3$, F, Cl, Br, OH, OCH$_3$, COOH, a radical of —CO—NH-L$_1$-Q$_2$ in which L$_1$ is a C$_2$-C$_4$ alkylene divalent radical and Q$_2$ is a (meth)acryloyloxy or (meth)acryloylamido group; and R$_3$, R$_4$, and R$_5$ independent of one other are H, CH$_3$, CCl$_3$, CF$_3$, F, Cl, Br, NO$_2$, OH, OCH$_3$, or NR'R" in which R' and R" independent of each other are H or C$_1$-C$_4$ alkyl;

provided that only one of R$_1$ and R$_2$ contains a (meth)acryloylamido or (meth)acryloyloxy group.

2. The UV-absorbing vinylic monomer of invention 1, wherein only one of R$_1$ and R$_2$ contains a (meth)acryloylamido group.

3. The UV-absorbing vinylic monomer of invention 1, wherein only one of R$_1$ and R$_2$ contains a (meth)acryloyloxy group.

4. The UV-absorbing vinylic monomer of invention 1, being selected from the group consisting of:

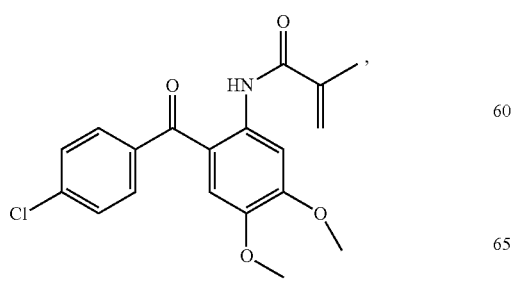

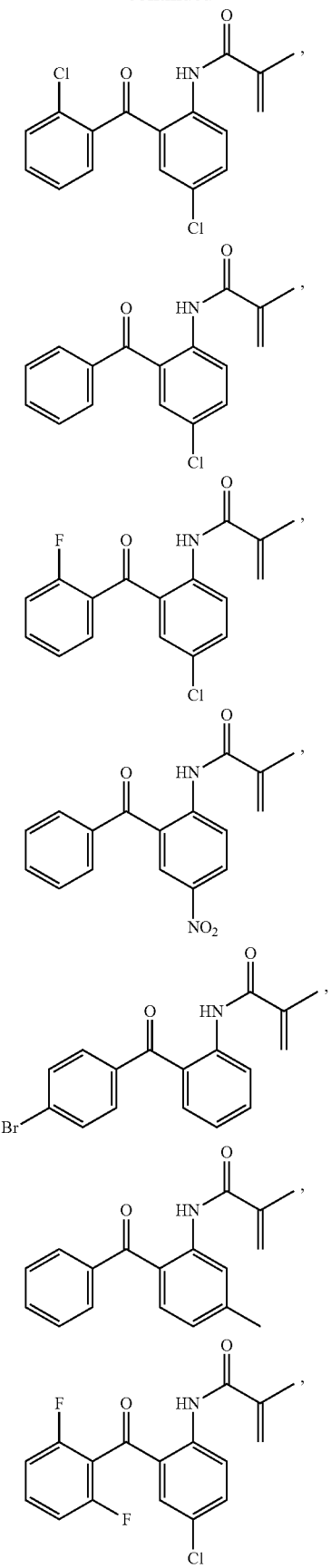

-continued
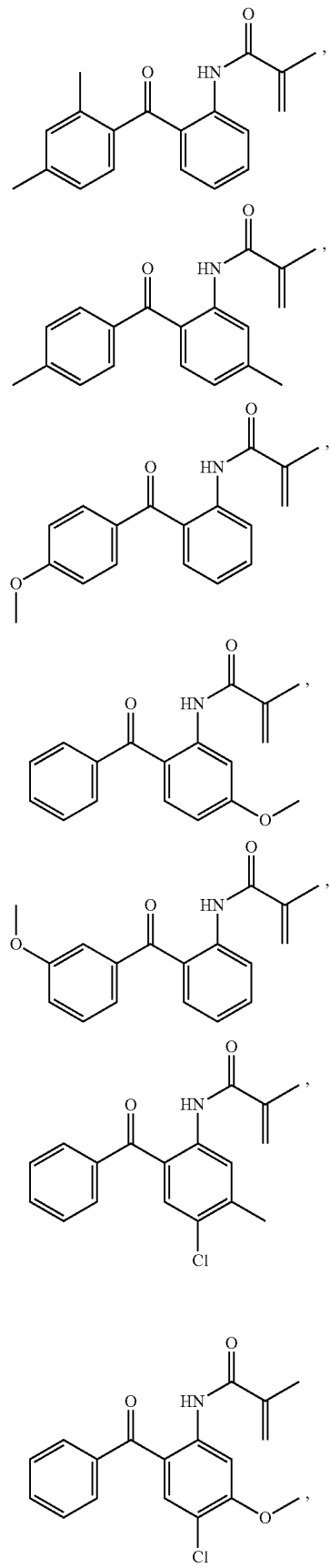
-continued
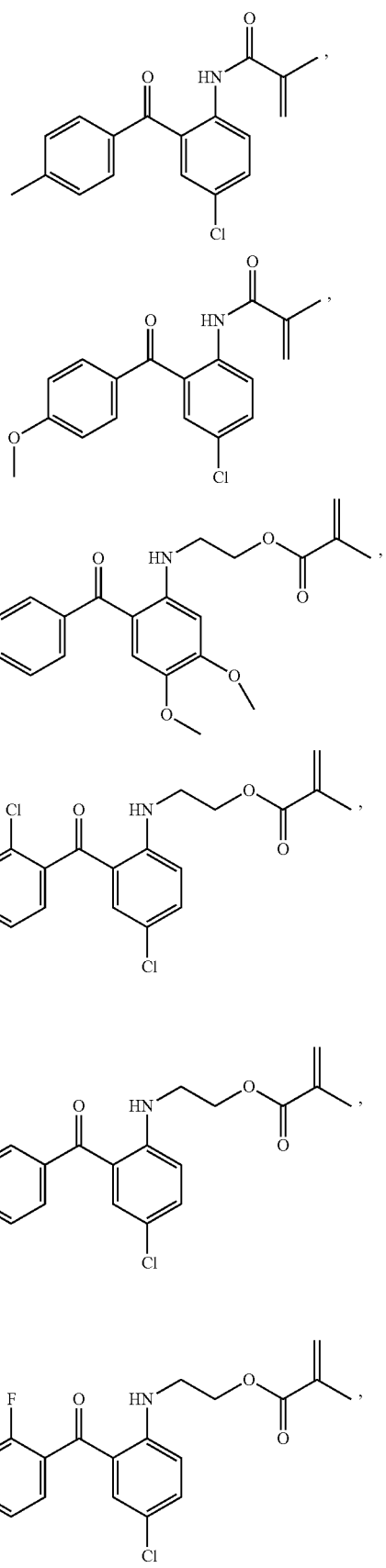

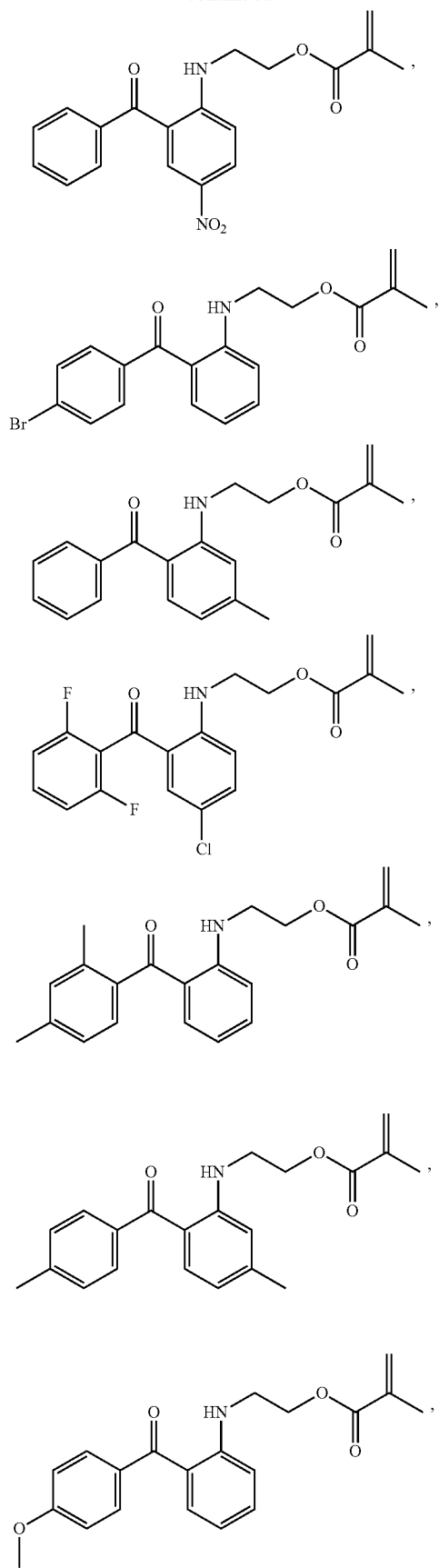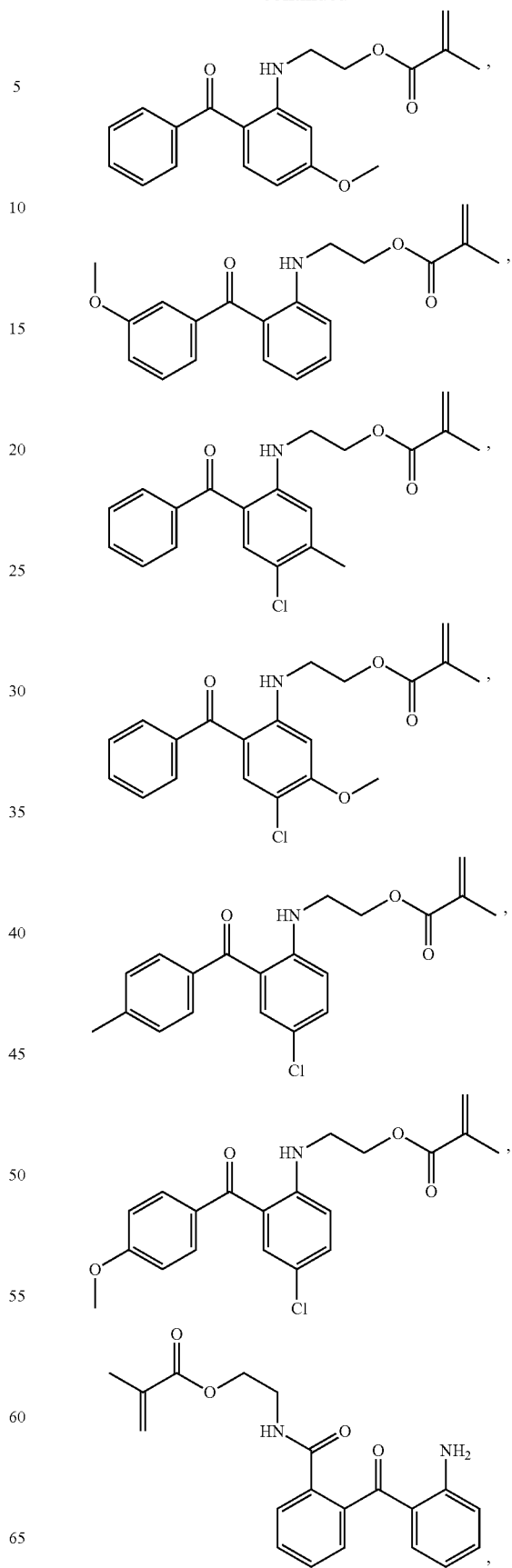

-continued

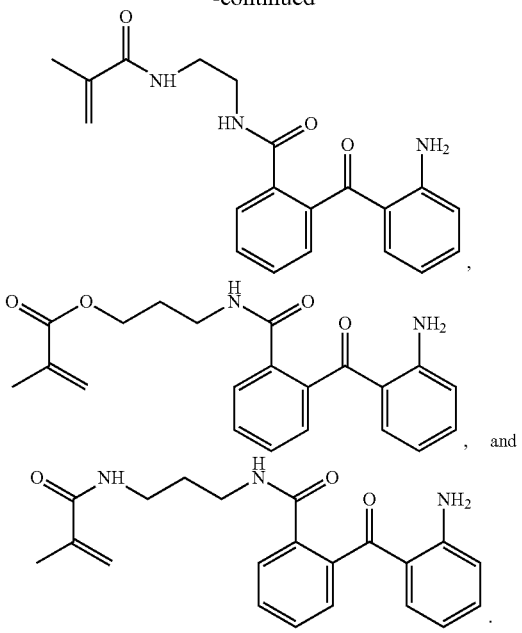

5. A contact lens comprising a crosslinked material which comprises monomeric units of a UV-absorbing vinylic monomer of any one of inventions 1 to 4.
6. The contact lens of invention 5, wherein the contact lens is a hydrogel contact lens.
7. The contact lens of invention 5, wherein the contact lens is a silicone hydrogel contact lens.
8. The contact lens of any one of inventions 5 to 7, wherein the contact lens has: an UVB transmittance of about 10% or less between 280 and 315 nanometers; a UVA transmittance of about 30% or less between 315 and 380 nanometers; and a water content of from about 15% to about 80% by weight (at room temperature, about 22° C. to 28° C.) when being fully hydrated.
9. The contact lens of invention 8, wherein the contact lens has an UVB transmittance of about 5% or less, preferably about 2.5% or less, more preferably about 1% or less between 280 and 315 nanometers.
10. The contact lens of invention 8 or 9, wherein the contact lens has a UVA transmittance of about 20% or less, preferably about 10% or less, more preferably about 5% or less between 315 and 380 nanometers.
11. The contact lens of any one of inventions 8 to 10, wherein the contact lens has a Violet transmittance of about 60% or less, preferably about 50% or less, more preferably about 40% or less, even more preferably about 30% or less between 380 nm and 440 nm.
12. The contact lens of any one of inventions 8 to 11, wherein the contact lens has a water content of from about 30% to about 75% by weight (at room temperature, about 22° C. to 28° C.) when being fully hydrated.
13. A method for producing UV-absorbing contact lenses, comprising the steps of:
   (1) obtaining a lens formulation comprising (a) a UV-absorbing vinylic monomer of formula (I) of any one of claims 1 to 4, (b) a free-radical initiator, and (c) at least one polymerizable component selected from the group consisting of a hydrophilic vinylic monomer, a hydrophobic vinylic monomer free of silicone, a vinylic crosslinking agent, a siloxane-containing vinylic monomer, a siloxane containing vinylic macromer, a water-soluble prepolymer free of silicone, and a siloxane-containing amphiphilic prepolymer;
   (2) introducing the lens formulation into a mold for making a soft contact lens, wherein the mold has a first mold half with a first molding surface defining the anterior surface of a contact lens and a second mold half with a second molding surface defining the posterior surface of the contact lens, wherein said first and second mold halves are configured to receive each other such that a cavity is formed between said first and second molding surfaces; and
   (3) curing thermally or actinically the lens formulation in the mold to crosslink the UV-absorbing vinylic monomer and the polymerizable component in the lens formulation to form the UV-absorbing contact lens, wherein the formed UV-absorbing contact lens comprises an anterior surface defined by the first molding surface and an opposite posterior surface defined by the second molding surface and is characterized by having the UVB transmittance of about 10% or less between 280 and 315 nanometers and a UVA transmittance of about 30% or less between 315 and 380 nanometers.
14. The method of invention 13, wherein the free-radical initiator is a thermal initiator, wherein the step of curing is carried out thermally.
15. The method of invention 13, wherein the free-radical initiator is a photoinitiator, wherein the step of curing is carried out by irradiation with a light having a wavelength within the range from 380 nm to 500 nm.
16. The method of invention 15, wherein the mold is a reusable mold, wherein the step of curing is carried out under a spatial limitation of radiation.
17. The method of any one of inventions 13 to 16, wherein the formed UV-absorbing contact lens has an UVB transmittance of about 5% or less, preferably about 2.5% or less, more preferably about 1% or less between 280 and 315 nanometers.
18. The method of any one of inventions 13 to 17, wherein the formed UV-absorbing contact lens has a UVA transmittance of about 20% or less, preferably about 10% or less, more preferably about 5% or less between 315 and 380 nanometers.
19. The method of any one of inventions 13 to 18, wherein the formed UV-absorbing contact lens has a Violet transmittance of about 60% or less, preferably about 50% or less, more preferably about 40% or less, even more preferably about 30% or less between 380 nm and 440 nm.
20. The method of any one of inventions 13 to 19, wherein the formed UV-absorbing contact lens has a water content of from about 30% to about 75% by weight (at room temperature, about 22° C. to 28° C.) when fully hydrated.

The previous disclosure will enable one having ordinary skill in the art to practice the invention. Various modifications, variations, and combinations can be made to the various embodiment described herein. In order to better enable the reader to understand specific embodiments and the advantages thereof, reference to the following examples is suggested. It is intended that the specification and examples be considered as exemplary.

EXAMPLE 1

Transmittance. Contact lenses are manually placed into a specially fabricated sample holder or the like which can maintain the shape of the lens as it would be when placing onto eye. This holder is then submerged into a 1 cm path-length quartz cell containing phosphate buffered saline (PBS, pH~7.0-7.4) as the reference. A UV/visible spectrophotmeter, such as, Varian Cary 3E UV-Visible Spectrophotometer with a LabSphere DRA-CA-302 beam splitter or the like, can be used in this measurement. Percent transmission spectra are collected at a wavelength range of 250-800 nm with % T values collected at 0.5 nm intervals. This data is transposed onto an Excel spreadsheet and used to determine if the lenses conform to Class 1 UV absorbance. Transmittance is calculated using the following equations:

$$UVA \% T = \frac{\text{Average } \% T \text{ between 380-316 nm}}{\text{Luminescence } \% T} \times 100$$

$$UVB \% T = \frac{\text{Average } \% T \text{ between 280-315 nm}}{\text{Luminescence } \% T} \times 100$$

$$\text{Violet } \% T = \frac{\text{Average } \% T \text{ between 440-380 nm}}{\text{Luminescence } \% T} \times 100$$

in which Luminescence % T (the percent transmittance) is the ratio of luminous flux transmitted by the lens to the incident luminous flux (ISO 13666:1998).

Photo-rheology: The photo-rheology experiment measures the elastic (G') and viscous modulus (G") as a function of time during curing. The experiment is conducted by using an appropriate light source, optionally cutoff filters to select wavelengths of interest, and a rheometer. The light source is a Mercury bulb in a Hamamatsu light source. The intensity of light source is set by adjusting the shutter opening to get an appropriate intensity measured by a radiometer. The sample is placed between a quartz plate that allows UV light to pass through and the rheometer. The cure time is determined when the elastic modulus (G') reaches a plateau.

EXAMPLE 2

Preparation of CE-PDMS Macromer

In the first step, α,ω-bis(2-hydroxyethoxypropyl)-polydimethylsiloxane (Mn=2000, Shin-Etsu, KF-6001a) is capped with isophorone diisocyanate (IPDI) by reacting 49.85 g of α,ω-bis(2-hydroxyethoxypropyl)-polydimethylsiloxane with 11.1 g IPDI in 150 g of dry methyl ethyl ketone (MEK) in the presence of 0.063 g of dibutyltindilaurate (DBTDL). The reaction is kept for 4.5 h at 40° C., forming IPDI-PDMS-IPDI. In the second step, a mixture of 164.8 g of α,ω-bis(2-hydroxyethoxypropyl)-polydimethylsiloxane (Mn=3000, Shin-Etsu, KF-6002) and 50 g of dry MEK are added dropwise to the IPDI-PDMS-IPDI solution to which has been added an additional 0.063 g of DBTDL. The reactor is held for 4.5 h at about 40° C., forming HO-PDMS-IPDI-PDMS-IPDI-PDMS-OH. MEK is then removed under reduced pressure. In the third step, the terminal hydroxyl-groups are capped with methacryloyloxyethyl groups in a third step by addition of 7.77 g of isocyanatoethylmethacrylate (IEM) and an additional 0.063 g of DBTDL, forming IEM-PDMS-IPDI-PDMS-IPDI-PDMS-IEM (i.e., CE-PDMS terminated with methacrylate groups).

Alternate Preparation of CE-PDMS Macromer with Terminal Methacrylate Groups 240.43 g of KF-6001 is added into a 1-L reactor equipped with stirring, thermometer, cryostat, dropping funnel, and nitrogen/vacuum inlet adapter, and then dried by application of high vacuum (2×10⁻² mBar). Then, under an atmosphere of dry nitrogen, 320 g of distilled MEK is then added into the reactor and the mixture is stirred thoroughly. 0.235 g of DBTDL is added to the reactor. After the reactor is warmed to 45° C., 45.86 g of IPDI are added through an addition funnel over 10 minutes to the reactor under moderate stirring. The reaction is kept for 2 hours at 60° C. 630 g of KF-6002 dissolved in 452 g of distilled MEK are then added and stirred until a homogeneous solution is formed. About 0.235 g of DBTDL is added, and the reactor is held at about 55° C. overnight under a blanket of dry nitrogen. The next day, MEK is removed by flash distillation. The reactor is cooled and 22.7 g of IEM are then charged to the reactor followed by about 0.235 g of DBTDL. After about 3 hours, an additional 3.3 g of IEM are added and the reaction is allowed to proceed overnight. The following day, the reaction mixture is cooled to about 18° C. to obtain CE-PDMS macromer with terminal methacrylate groups.

EXAMPLE 3

Synthesis of N-(2-benzoyl-4-chlorophenyl)methacrylamide

In a 500 mL Erlenmyer flask equipped with a magnetic stirrer was added 300 mL chloroform, 25.1 g (108 mmol) (2-amino-5-chlorophenyl)(phenyl)methanone, 21.2 g (138 mmol) methacrylic anhydride, 20 g pyridine, 1 drop stannous octoate (Aldrich), and 50 mg 4-methoxyphenol (Aldrich). The reaction mixture was stirred at ambient temperature for 3 days, then 50° C. for 1 day. TLC (70/30 hexanes/acetone) still showed unreacted starting material. An additional 20.58 g methacrylic anhydride was added. The solution was heated at 50° C. for an additional 5 hours. 400 ml dichloromethane was added and the mixture was washed with ~2M sodium bicarbonate (3×1 L) and then ~2M NaCl (1×1 L). The organic layer was dried with sodium sulfate and the solvent removed under reduced pressure to afford orange oil which crystallized upon sitting at ambient temperature. Prior to crystallizing, aliquots were dissolved in vials containing IPA, methanol, ethanol, toluene, and diethyl ether. IPA was the best recrystallization solvent. Recrystallization also took place readily in diethyl ether and methanol, but not toluene. The crude crystallized product was cooled for several hours at −20° C. and then cold (−20° C.) ethanol was added and the product was filtered. The yellow solid was recrystallized in IPA to afford 15.22 g (47%) of yellow needles. ¹H NMR spectrum in CDCl₃ was consistent with structure (δ=11.3 ppm, 1H, N—H; δ=7.4-8.9 ppm, 8H, aromatic protons; δ=5.5 and 6.0 ppm, 2H, vinyl protons; δ=2.1 ppm, 3H, alpha-methyl protons.

EXAMPLE 4

Two lens formulations (4A and 4B) are prepared from the following components: L-PEG 2000 (N-(carbonyl-methoxypolyethylene glycol-2000)-1,2-disteaoyl-sn-glycero-3-phosphoethanolamin, sodium salt; CE-PDMS (chain-extended polydimethylsiloxane crosslinker prepared in Example 2); DMA (N,N-dimethylacrylamide); TRIS-Am (N-[tris(trimethylsiloxy)-silylpropyl]acrylamide); Ge—Pl (Bis(4-methoxybenzoyl) diethyl germanium); DMPC (1,2-Dimyristoyl-sn-glycero-3-phosphorcholine); Darocur 1173 (2-Hydroxy-2-methylpropiophenone); UV-absorbing vinylic monomer (prepared in Example 3), to have the compositions shown in the following Table.

| Ingredient | Composition (% by weight) | |
|---|---|---|
| | Formulation 4A | Formulation 4B |
| LPEG2000 | 0.61 | 0.61 |
| DMPC | 0.76 | 0.76 |
| UV-absorbing vinylic monomer of Example 3 | 0.5 | — |
| CE PDMS of Example 2 | 31.83 | 31.83 |
| Tris acrylamide | 20.21 | 20.71 |
| DMA | 23.24 | 23.24 |
| Ge PI | 0.6 | — |
| Darocur 1173 | — | 1.01 |
| 1-propanol | 22.25 | 21.84 |

EXAMPLE 5

PAA-coating Solution.

A polyacrylic acid (PAA) coating solution is prepared by dissolving an amount of PAA (M.W.: 450 kDa, from Lubrizol) in a given volume of 1-propanol (1-PrOH) to have a concentration of about 0.44% by weight and the pH is adjusted with formic acid to about 2.0.

Preparation of In-Package-Coating solution (IPC Saline).

Poly(AAm-co-AA)(90/10) partial sodium salt (~90% solid content, poly(AAm-co-AA) 90/10, Mw 200,000) is purchased from Polysciences, Inc. and used as received. Polyamidonamine epichlorohydrin (PAE) (Kymene, an azetidinium content of 0.46 assayed with NMR) is purchased from Ashland as an aqueous solution and used as received. IPC saline is prepared by dissolving about 0.07% w/w of poly(AAm-co-AA)(90/10) and about 0.15% of PAE (an initial azetidinium millimolar equivalents of about 8.8 millimole) in phosphate-buffered saline (PBS) (about 0.044 w/w % $NaH_2PO_4.H_2O$, about 0.388 w/w/c/% $Na_2HPO_4.2H_2O$, about 0.79 w/w % NaCl) and adjusting the pH to 7.2~7.4. Then the IPC saline is heat pre-treated for about 4 hours at about 70° C. (heat pretreatment). During this heat pretreatment, poly(AAm-co-AA) and PAE are partially crosslinked to each other (i.e., not consuming all azetidinium groups of PAE) to form a water-soluble and thermally-crosslinkable hydrophilic polymeric material containing azetidinium groups within the branched polymer network in the IPC saline. After the heat pre-treatment, the IPC is cooled to room temperature then filtered using a 0.22 micron PES membrane filter.

Lens Fabrication Using Formulation 4A from Example 4

Lenses are prepared by cast-molding from the lens formulation prepared above in a reusable mold (quartz female mold half and glass male mold half), similar to the mold shown in FIGS. 1-6 in U.S. Pat. Nos. 7,384,590 and 7,387,759 (FIGS. 1-6). Lens formulation 4A prepared in Example 4 in the molds is irradiated for about 25 seconds using a 450 nm LED lamp. The measured total intensity from 350 to 500 nm is 50 mW/cm². Cast-molded contact lenses are then extracted by dipping in the following series of baths: deionized (DI) water bath (about 56 seconds); 3 methyl ethyl ketone (MEK) baths (about 22, 78, 224 seconds respectively, (DI) water bath (about 56 seconds). After lens extraction, the lenses are in contact for 44 seconds with the PAA-coating solution prepared above to form a PAA coating on each lens, then equilibrated into water, and then placed into polypropylene shells containing 0.65 mL of IPC saline prepared above, and autoclaved for 45 minutes at 121° C. The UV/Vis spectrum is shown in FIG. 1A.

Lens Fabrication Using Formulation 4B from Example 4

Lenses are prepared by cast-molding from the lens formulation prepared above in a reusable mold (quartz female mold half and glass male mold half), similar to the mold shown in FIGS. 1-6 in U.S. Pat. Nos. 7,384,590 and 7,387,759 (FIGS. 1-6). Lens formulation 4B prepared in Example 4 in the molds is irradiated for about 25 seconds using a Hamamatsu lamp with the light below 328 nm blocked by a long pass filter. The measured total intensity from 310 to 400 nm is 50 mW/cm². Cast-molded contact lenses are then extracted by dipping in the following series of baths: deionized (DI) water bath (about 56 seconds); 3 methyl ethyl ketone (MEK) baths (about 22, 78, 224 seconds respectively, (DI) water bath (about 56 seconds). After lens extraction, the lenses are in contact for 44 seconds with the PAA-coating solution prepared above to form a PAA coating on each lens, then equilibrated into water, and then placed into polypropylene shells containing 0.65 mL of IPC saline prepared above, and autoclaved for 45 minutes at 121° C. The UV/Vis spectrum is shown in FIG. 1B.

What is claimed is:

1. A UV-absorbing vinylic monomer, being selected from the group consisting of:

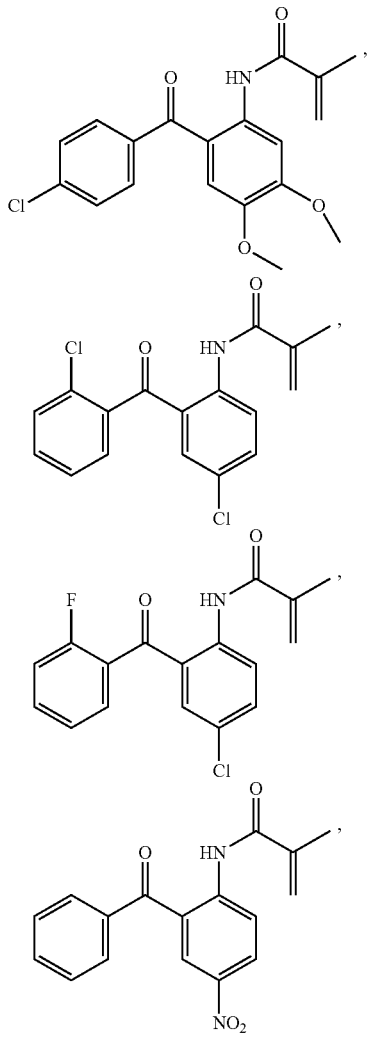

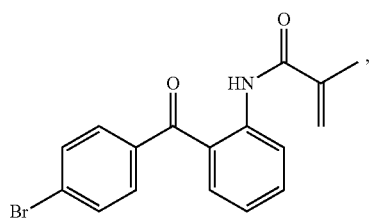
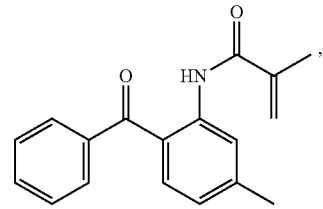
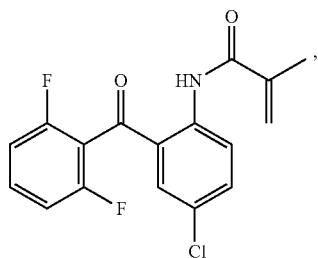
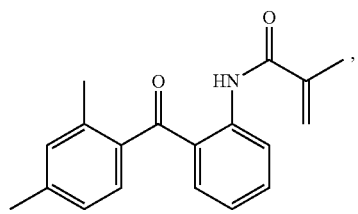
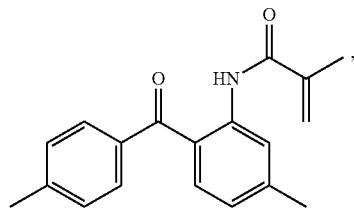
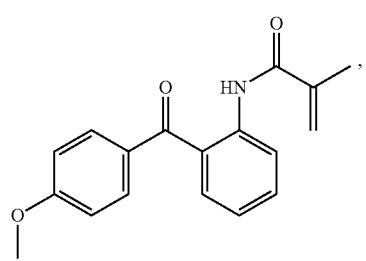
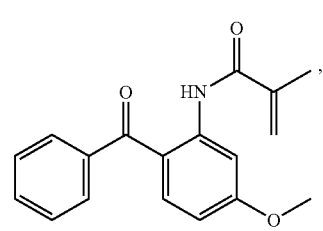
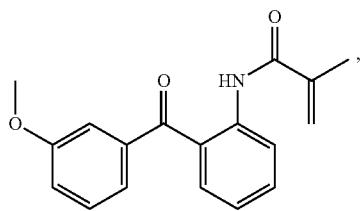
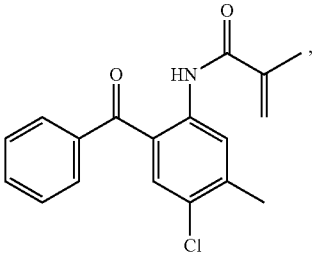
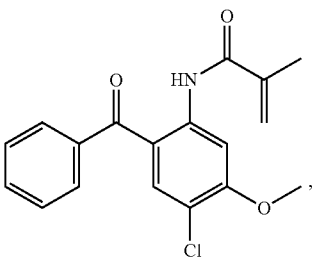
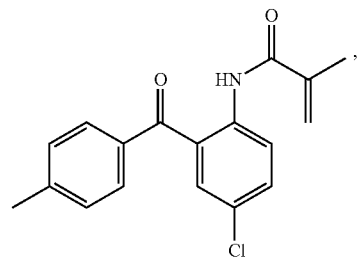
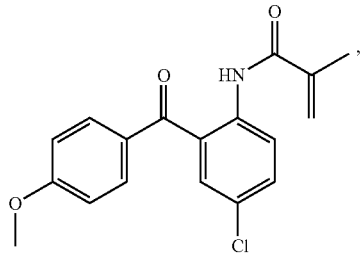
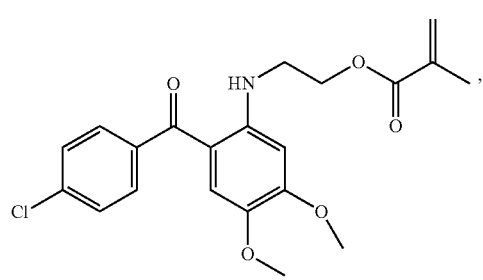

-continued
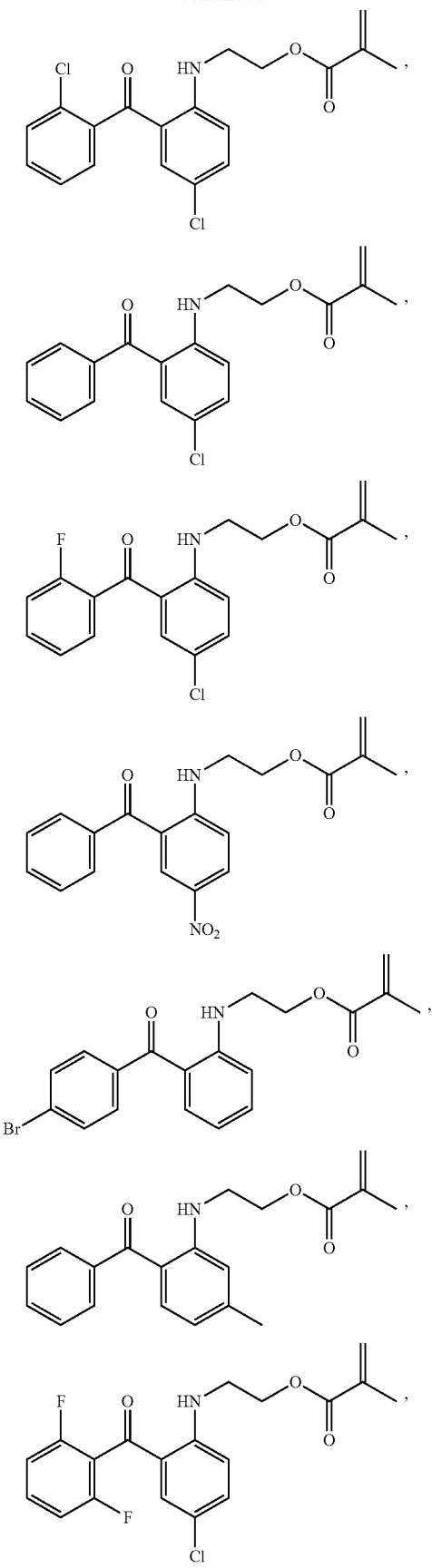
-continued
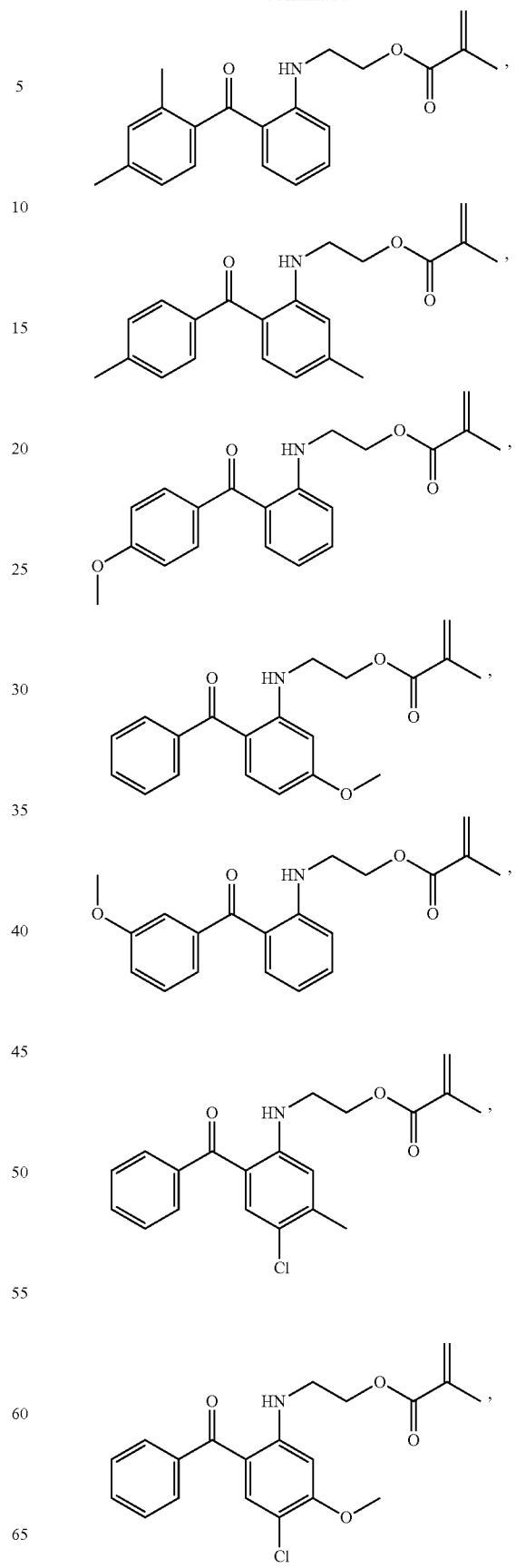

-continued
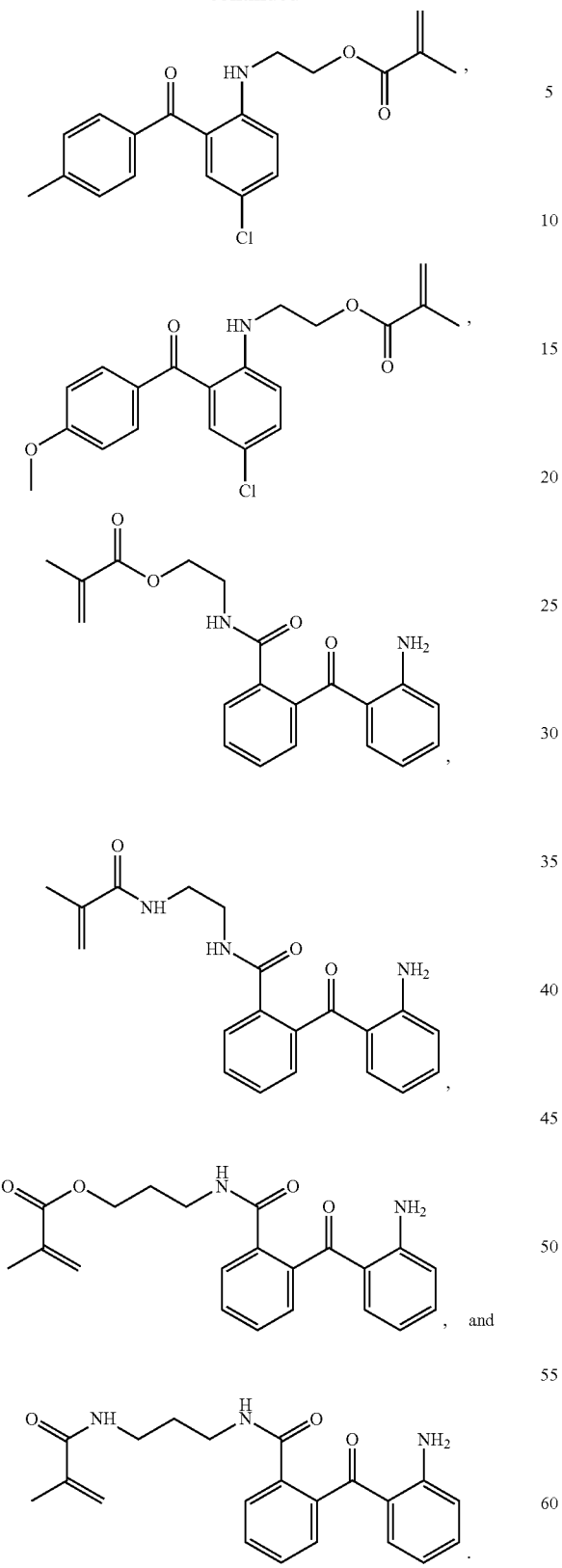
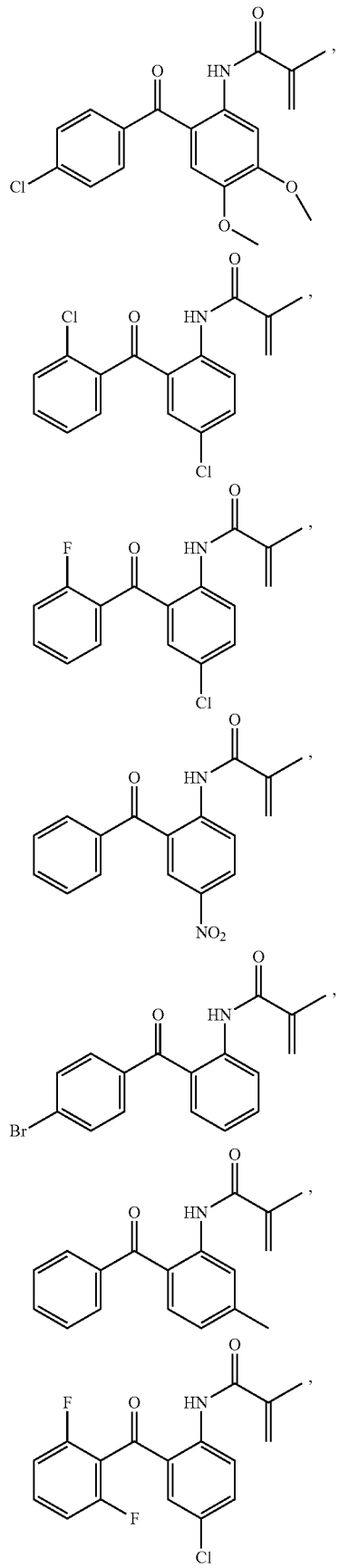
2. A contact lens comprising a crosslinked material which comprises monomeric units of a UV-absorbing vinylic monomer selected from the group consisting of:

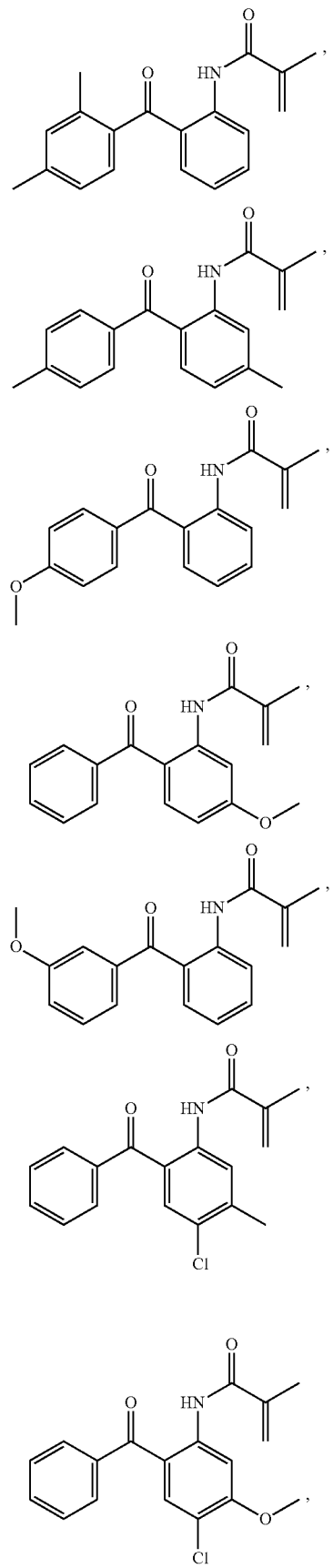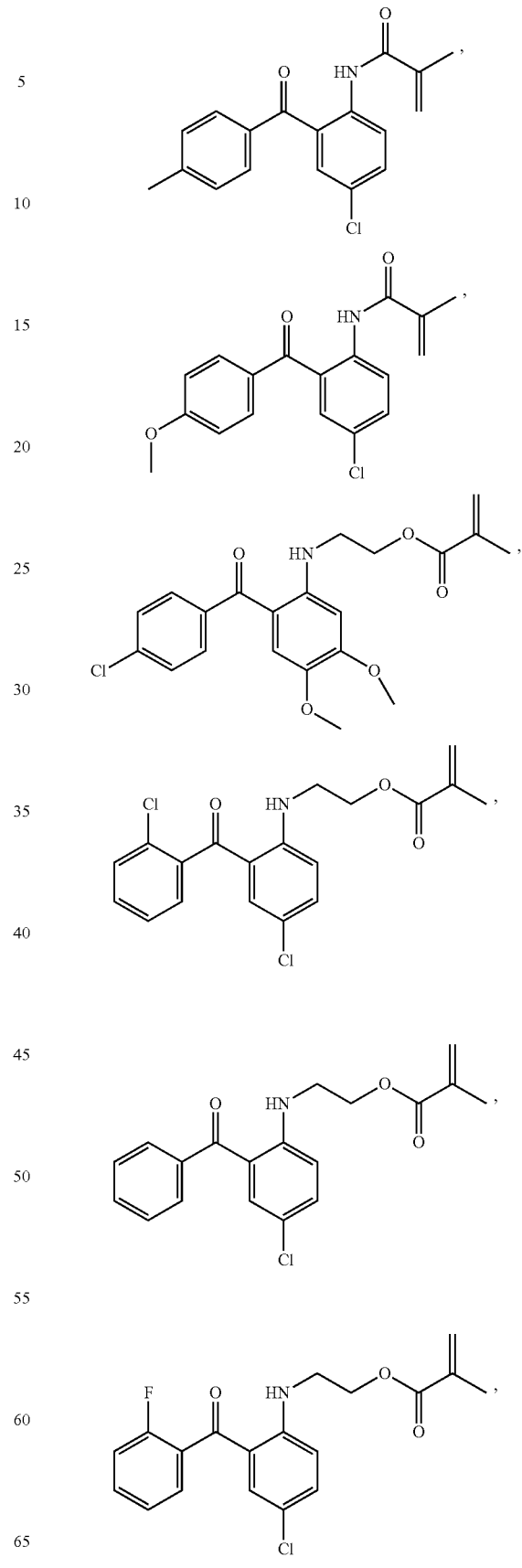

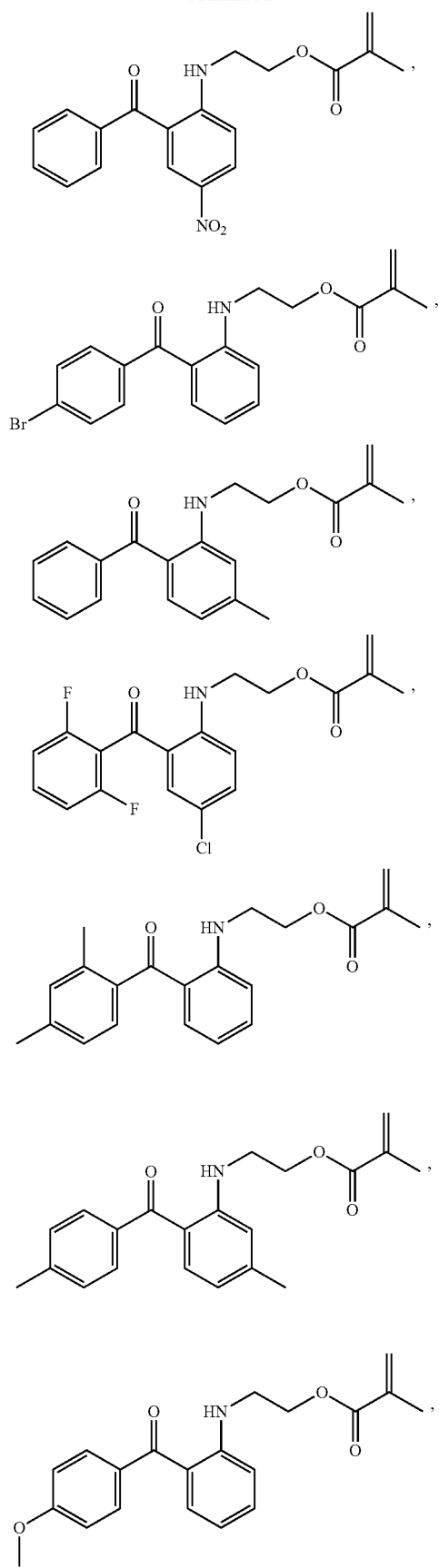
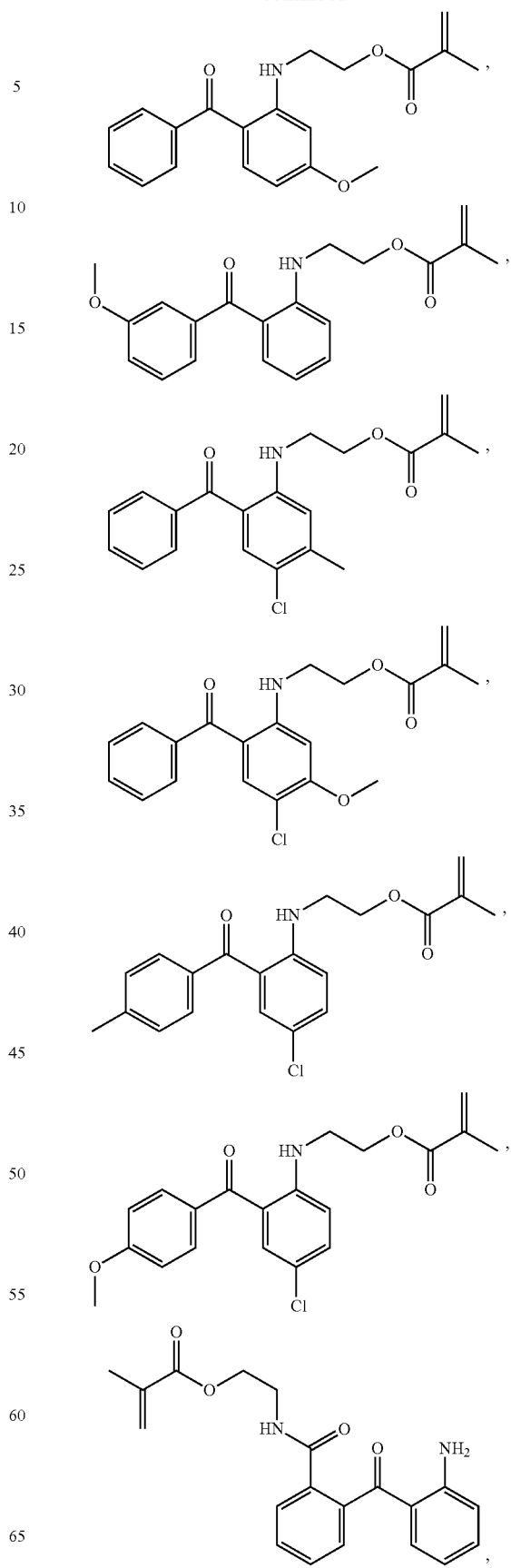

-continued

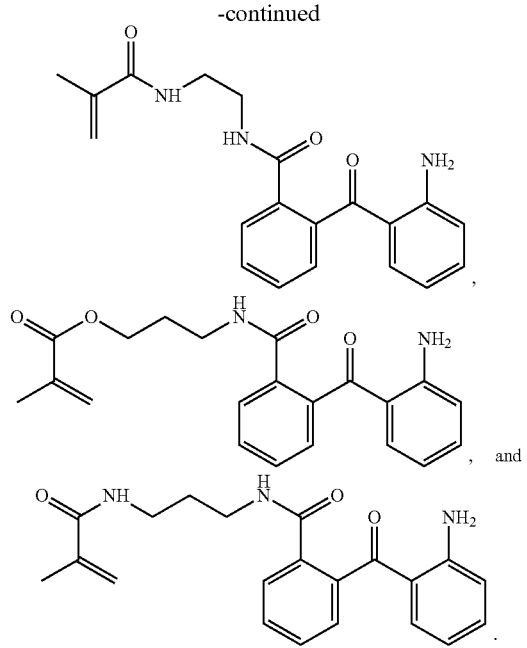

, and

3. The contact lens of claim 2, wherein the contact lens is a hydrogel contact lens.

4. The contact lens of claim 2, wherein the contact lens is a silicone hydrogel contact lens.

5. The contact lens of claim 2, wherein the contact lens has: an UVB transmittance of about 10% or less between 280 and 315 nanometers; a UVA transmittance of about 30% or less between 315 and 380 nanometers; a Violet transmittance of about 60% or less between 380 nm and 440 nm; and a water content of from about 15% to about 80% by weight (at room temperature, about 22° C. to 28° C.) when being fully hydrated.

6. A method for producing UV-absorbing contact lenses, comprising the steps of:

(1) obtaining a lens formulation comprising (a) a UV-absorbing vinylic monomer selected from the group consisting of

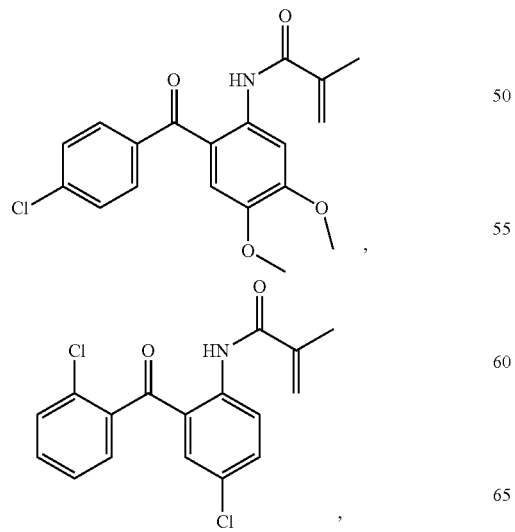

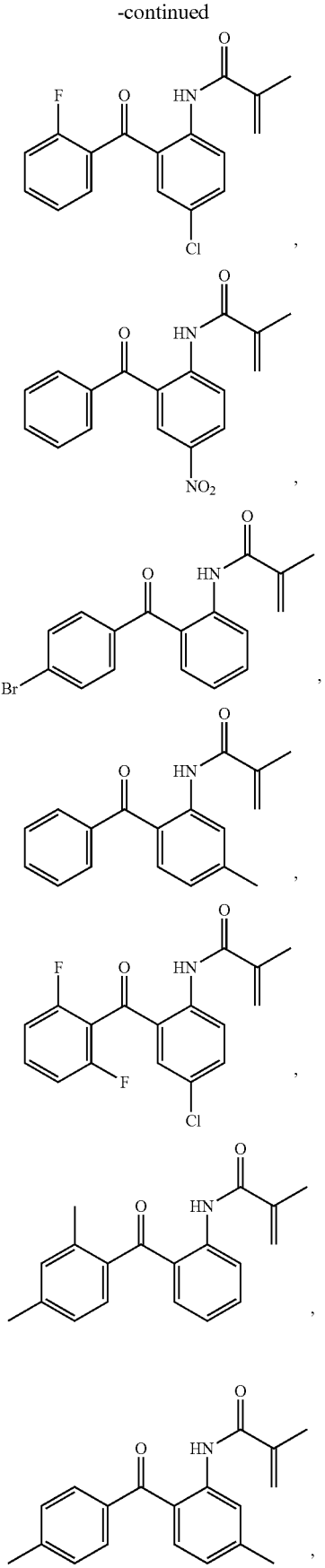

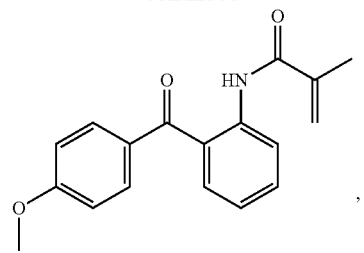,
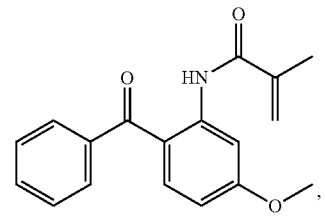,
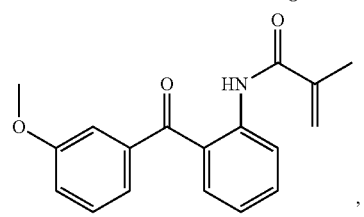,
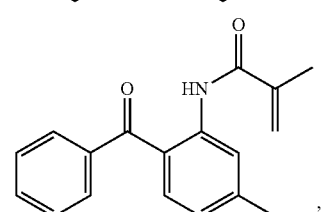,
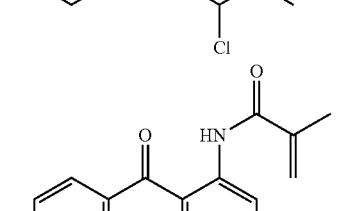,
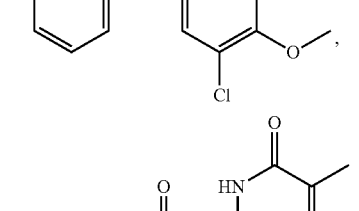,
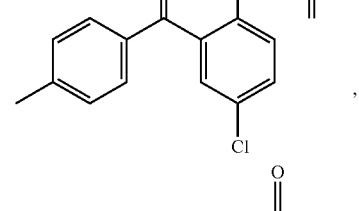,
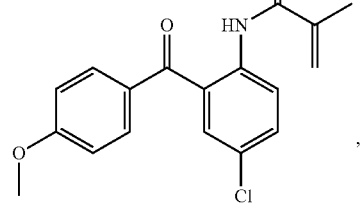,
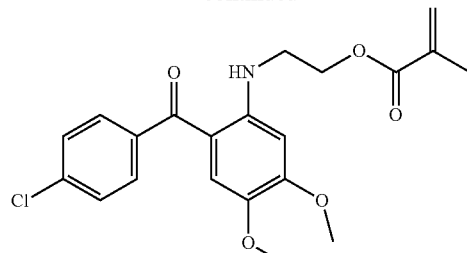,
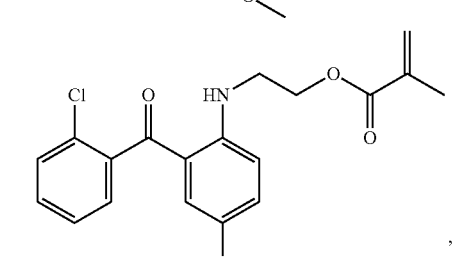,
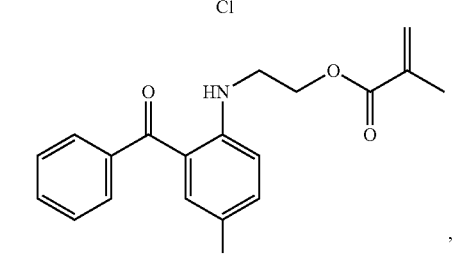,
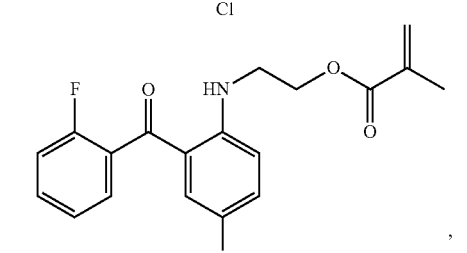,
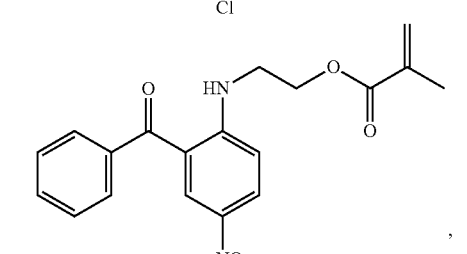,
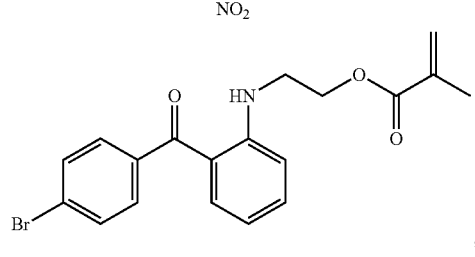,
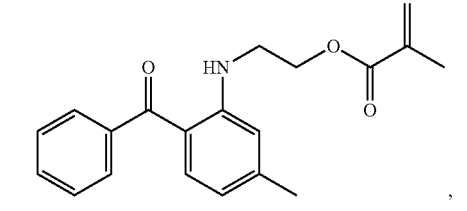,

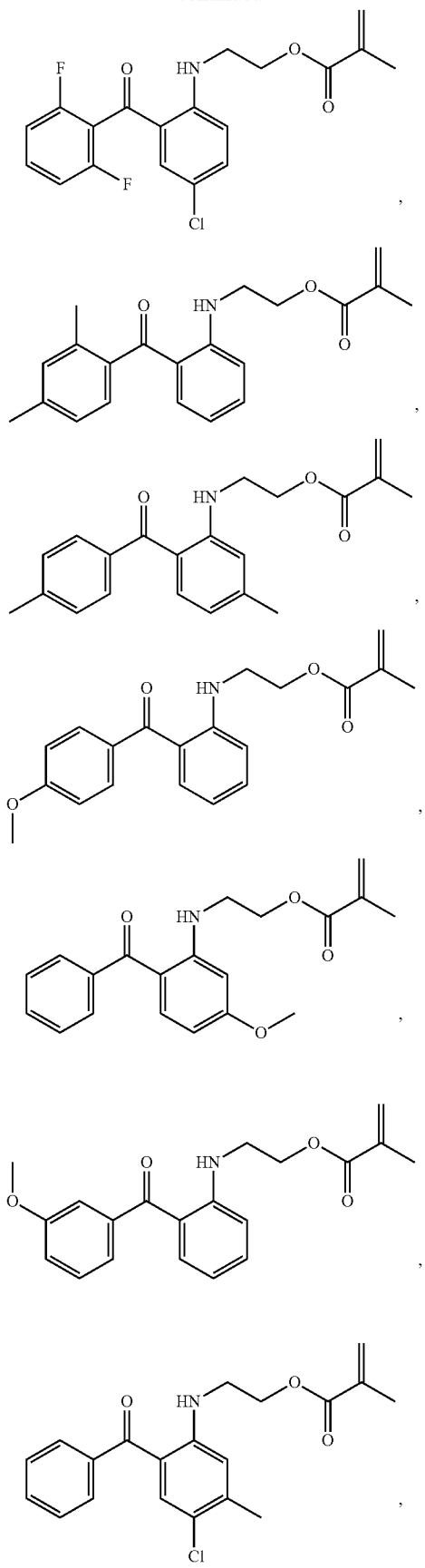
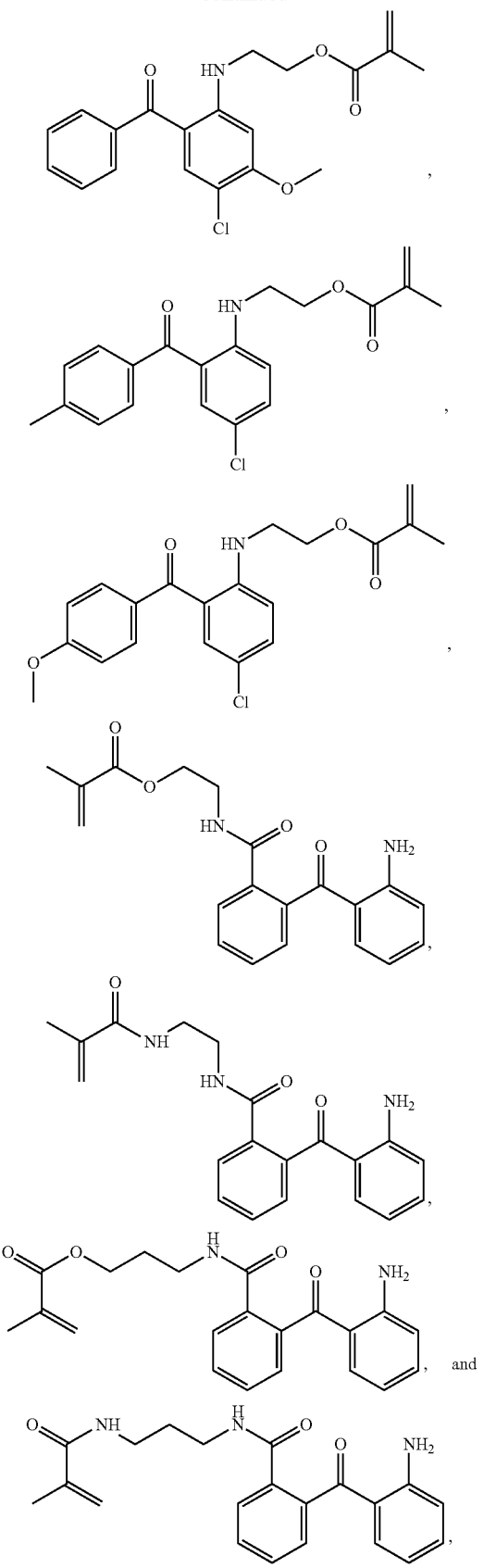

(b) a free-radical initiator, and
(c) at least one polymerizable component selected from the group consisting of a hydrophilic vinylic monomer, a hydrophobic vinylic monomer free of silicone, a vinylic crosslinking agent, a siloxane-containing vinylic monomer, a siloxane containing vinylic macromer, a water-soluble prepolymer free of silicone, and a siloxane-containing amphiphilic prepolymer;

(2) introducing the lens formulation into a mold for making a soft contact lens, wherein the mold has a first mold half with a first molding surface defining the anterior surface of a contact lens and a second mold half with a second molding surface defining the posterior surface of the contact lens, wherein said first and second mold halves are configured to receive each other such that a cavity is formed between said first and second molding surfaces; and (3) curing thermally or actinically the lens formulation in the mold to crosslink the UV-absorbing vinylic monomer and the polymerizable component in the lens formulation to form the UV-absorbing contact lens, wherein the formed UV-absorbing contact lens comprises an anterior surface defined by the first molding surface and an opposite posterior surface defined by the second molding surface and is characterized by having the UVB transmittance of about 10% or less between 280 and 315 nanometers, a UVA transmittance of about 30% or less between 315 and 380 nanometers, and a Violet transmittance of about 60% or less between 380 nm and 440 nm.

7. The method of claim 6, wherein the free-radical initiator is a thermal initiator, wherein the step of curing is carried out thermally.

8. The method of claim 6, wherein the free-radical initiator is a photoinitiator, wherein the step of curing is carried out by irradiation with a light having a wavelength within the range from 380 nm to 500 nm.

9. The method of claim 8, wherein the mold is a reusable mold, wherein the step of curing is carried out under a spatial limitation of radiation.

\* \* \* \* \*